United States Patent [19]
Habeshaw et al.

[11] Patent Number: 5,935,579
[45] Date of Patent: Aug. 10, 1999

[54] AIDS THERAPY AND VACCINE

[75] Inventors: John Anthony Habeshaw, Harpenden; Angus George Dalgleish, London; Elizabeth Hounsell, Isleworth; Lynne Bountiff, Aylebury, all of United Kingdom

[73] Assignee: Retroscreen Limited, Whitechapel, United Kingdom

[21] Appl. No.: 08/323,686

[22] Filed: Oct. 14, 1994

Related U.S. Application Data

[63] Continuation of application No. 07/766,366, Sep. 25, 1991, abandoned.

[30] Foreign Application Priority Data

Sep. 25, 1990 [GB] United Kingdom ............... 9020999
Oct. 15, 1990 [GB] United Kingdom ............... 9022330
Mar. 27, 1991 [GB] United Kingdom ............... 9106540

[51] Int. Cl.$^6$ ................ A61K 39/21; A61K 39/38; A61K 39/12; A61K 38/00
[52] U.S. Cl. ................ 424/188.1; 424/184.1; 424/204.1; 424/208.1; 530/300; 530/327; 530/350; 530/388.1
[58] Field of Search ............ 424/188.1, 204.1, 424/184.1, 208.1; 530/350, 388.1, 300, 327

[56] References Cited

U.S. PATENT DOCUMENTS 4,943,628  7/1990  Rosen et al. ............... 530/326

FOREIGN PATENT DOCUMENTS 0317804  5/1989  European Pat. Off. .
8904370  5/1989  WIPO .

OTHER PUBLICATIONS

Golding, et al., J. of Experimental Med., 167:914–923 (Mar. 1988).
Palker, et al, 1987, "A Conserved Region at the COOH Terminus . . . " PNAS 84: 2479–2483.
Yourno, et al, 1988, "Nucleotide Sequence Analysis of the Env . . . " AIDS Res. Hum. Retro. 4(3):165–73.
Helseth, et al, 1991, "Human Immunodeficiency Virus Type 1 sp120 Enevelope Glycoprotein Regions Important for Association with gp41 Transmembrane Glycoprotein" J. Virology 65(4):2119–2123.
Anand, et al, 1989, "Biological and Molecular Characterization of Human Immunodeficiency Virus (HIV–$1_{Br}$) from the Brain of a Patient with Progressive Dementia". Virology 168: 79–89.
Cohen, 1993, "Jitters Jeopardize AIDS . . . " Science 262: 980–981.
Butini, et al, 1994, "Comparative Analysis of HIV . . . " J. Cellular Biochemistry, Suppl. 18B, Abstract J306.
Fox, 1994, "No Winners Against AIDS" Biotechnology 12: 128.
Helseth, et al, 1991, "Human Immunodeficiency Virus Type . . . " J. Virol. 65(4):2119–2123.
Vega, et al, 1990, "Autoimmune Response in AIDS" Nature 345:26.
Greene, 1993, "AIDS and the Immune System" Scientific American Sep. 1993, pp. 99–105.
Brown, 1993, "AIDS Vaccine Trials . . . " The Wash. Post. Newspaper, Jun. 10, 1993.

*Primary Examiner*—Frank C. Eisenschenk
*Assistant Examiner*—Brett Nelson
*Attorney, Agent, or Firm*—Hale and Dorr LLP

[57] ABSTRACT

The present invention provides therapy and prophylaxis against HIV-induced AIDS, as well as methods for ascertaining the susceptibility of an individual to HIV-induced AIDS, the invention being based on the discovery that AIDS results from gp120 of HIV mimicking the antigen-presenting component of the immune system, thereby spuriously activating certain CD4+ T cells in susceptible individuals, leading to a condition similar to graft versus host disease, the condition being treatable by eliminating the responsible T cells, for example.

9 Claims, 7 Drawing Sheets

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO:1:

Thr Lys Ala Lys Arg Arg Val Val Glu Arg Glu Lys Arg
    1               5                   10

(2) INFORMATION FOR SEQ ID NO:2:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:2:

Val Ala Glu Gln Leu Arg Ala Tyr Leu Glu Gly Thr Cys Val
    1               5                   10

(2) INFORMATION FOR SEQ ID NO:3:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:3:

Leu Leu Glu Gln Arg Arg Ala Ala Val Asp Thr Tyr Cys Arg
    1               5                   10

(2) INFORMATION FOR SEQ ID NO:4:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO:4:

Thr Arg Ala Lys Arg Arg Val Val Glu Arg Glu Lys Arg
    1             5                   10

(2) INFORMATION FOR SEQ ID NO:5:

(i) SEQUENCE CHARACTERISTICS:
        (A) LENGTH: 22 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 7
        (D) OTHER INFORMATION: /note= "This position is R or K."

(ix) FEATURE:
        (A) NAME/KEY: Modified-site
        (B) LOCATION: 9
        (D) OTHER INFORMATION: /note= "This position is V or I."

(xi) SEQUENCE DESCRIPTION: SEQ ID NO:5:

Gln Cys Thr His Gly Ile Xaa Pro Xaa Val Ser Thr Gln Leu Leu Leu
    1             5                  10              15

Asn Gly Ser Leu Ala Glu
                   20

(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:6:

Tyr Ala Pro Pro Ile
    1             5

(2) INFORMATION FOR SEQ ID NO:7:

(i) SEQUENCE CHARACTERISTICS:
        (A) LENGTH: 13 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 6
        (D) OTHER INFORMATION: /note= "This position is L or I."

(ix) FEATURE:
        (A) NAME/KEY: Modified-site
        (B) LOCATION: 7
        (D) OTHER INFORMATION: /note= "This position is L or I."

(xi) SEQUENCE DESCRIPTION: SEQ ID NO:7:

Ser Asn Ile Thr Gly Xaa Xaa Leu Thr Arg Asp Gly Gly
    1             5                  10

(2) INFORMATION FOR SEQ ID NO:8:

(i) SEQUENCE CHARACTERISTICS:
        (A) LENGTH: 9 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 4
        (D) OTHER INFORMATION: /note= "This position is D or N."

(ix) FEATURE:
        (A) NAME/KEY: Modified-site
        (B) LOCATION: 6
        (D) OTHER INFORMATION: /note= "This position is R or K."

(xi) SEQUENCE DESCRIPTION: SEQ ID NO:8:

Gly Gly Gly Xaa Met Xaa Asp Asn Trp
    1          5

(2) INFORMATION FOR SEQ ID NO:9:

(i) SEQUENCE CHARACTERISTICS:
        (A) LENGTH: 8 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 8
        (D) OTHER INFORMATION: /note= "This position is V or I."

(xi) SEQUENCE DESCRIPTION: SEQ ID NO:9:

Glu Leu Tyr Lys Tyr Lys Val Xaa
    1          5

(2) INFORMATION FOR SEQ ID NO:10:

(i) SEQUENCE CHARACTERISTICS:
        (A) LENGTH: 21 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 6
        (D) OTHER INFORMATION: /note= "This position is V or I."

(ix) FEATURE:
        (A) NAME/KEY: Modified-site
        (B) LOCATION: 10
        (D) OTHER INFORMATION: /note= "This position is R or K."

(ix) FEATURE:
        (A) NAME/KEY: Modified-site
        (B) LOCATION: 17
        (D) OTHER INFORMATION: /note= "This position is Q or E."

(xi) SEQUENCE DESCRIPTION: SEQ ID NO:10:

Ile Glu Pro Leu Gly Xaa Ala Pro Thr Xaa Ala Lys Arg Arg Val Val
    1          5                  10                15

Xaa Arg Glu Lys Arg
              20

(2) INFORMATION FOR SEQ ID NO:11:

(i) SEQUENCE CHARACTERISTICS:
        (A) LENGTH: 4 amino acids (B) TYPE: amino acid
        (C) STRANDEDNESS: single
        (D) TOPOLOGY: linear (xi) SEQUENCE DESCRIPTION: SEQ ID NO:11:

Ser Asn Ile Thr
    1

(2) INFORMATION FOR SEQ ID NO:12:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:12:

Val Val Pro Ser Gly Gln Glu Gln Arg Tyr
    1               5                   10

(2) INFORMATION FOR SEQ ID NO:13:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:13:

Val Val Ser Thr Gly Leu Ile Gln Asn Gly
    1               5                   10

(2) INFORMATION FOR SEQ ID NO:14:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:14:

Val Val Ser Thr Gln Leu Leu Asn Gly
    1               5

(2) INFORMATION FOR SEQ ID NO:15:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO:15:

Cys His Val Gln His Glu Gly Leu Pro Lys Pro Leu
    1               5                   10

(2) INFORMATION FOR SEQ ID NO:16:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO:16:

Cys Gln Val Glu His Pro Ser Val Thr Ser Pro Leu
    1               5                   10

(2) INFORMATION FOR SEQ ID NO:17:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:17:

Glu Phe Phe Tyr
    1

(2) INFORMATION FOR SEQ ID NO:18:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:18:

Ala Ala Asp Met
    1

(2) INFORMATION FOR SEQ ID NO:19:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:19:

Gly Gly Asp Met
    1

(2) INFORMATION FOR SEQ ID NO:20:

(i) SEQUENCE CHARACTERISTICS:
        (A) LENGTH: 22 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 6
        (D) OTHER INFORMATION: /note= "This position is V or I."

(ix) FEATURE:
        (A) NAME/KEY: Modified-site
        (B) LOCATION: 10
        (D) OTHER INFORMATION: /note= "This position is R or K."

(ix) FEATURE:
        (A) NAME/KEY: Modified-site
        (B) LOCATION: 17
        (D) OTHER INFORMATION: /note= "This position is Q or E."

(xi) SEQUENCE DESCRIPTION: SEQ ID NO:20:

Ile Glu Pro Leu Gly Xaa Ala Pro Thr Xaa Ala Lys Arg Arg Val Val
    1              5                     10                 15

Xaa Arg Glu Lys Arg Ala
              20

(2) INFORMATION FOR SEQ ID NO:21:

(i) SEQUENCE CHARACTERISTICS:
        (A) LENGTH: 4 amino acids
        (B) TYPE: amino acid
        (C) STRANDEDNESS: single (D) TOPOLOGY: linear (xi) SEQUENCE DESCRIPTION: SEQ ID NO:21:

Val Val Ser Ser
    1

(2) INFORMATION FOR SEQ ID NO:22:

(i) SEQUENCE CHARACTERISTICS:
        (A) LENGTH: 4 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 2
        (D) OTHER INFORMATION: /note= "X is undefined."

(xi) SEQUENCE DESCRIPTION: SEQ ID NO:22:

Tyr Xaa Pro Pro
    1

(2) INFORMATION FOR SEQ ID NO:23:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:23:

Val Val Lys Arg
    1

(2) INFORMATION FOR SEQ ID NO:24:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:24:

Thr Ala Ala Asp Met
    1               5

(2) INFORMATION FOR SEQ ID NO:25:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:25:

Val Ala Glu Gln Leu Arg Ala Tyr Leu Glu Gly Thr Cys Val
    1               5                   10

(2) INFORMATION FOR SEQ ID NO:26:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:26:

Leu Leu Glu Gln Arg Arg Ala Ala Val Asp Thr Tyr Cys Arg

```
            1               5                  10
```

(2) INFORMATION FOR SEQ ID NO:27:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO:27:

```
   Thr Lys Ala Lys Arg Arg Val Val Gln Arg Glu Lys Arg
   1               5                  10
```

(2) INFORMATION FOR SEQ ID NO:28:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO:28:

```
   Thr Lys Ala Lys Arg Arg Val Val Gln Arg Glu Lys Arg
   1               5                  10
```

(2) INFORMATION FOR SEQ ID NO:29:

(i) SEQUENCE CHARACTERISTICS:
        (A) LENGTH: 13 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 2
        (D) OTHER INFORMATION: /note= "This position is R or K."

(ix) FEATURE:
        (A) NAME/KEY: Modified-site
        (B) LOCATION: 9
        (D) OTHER INFORMATION: /note= "This position is E or Q."

(xi) SEQUENCE DESCRIPTION: SEQ ID NO:29:

```
   Thr Xaa Ala Lys Arg Arg Val Val Xaa Arg Glu Lys Arg
   1               5                  10
```

(2) INFORMATION FOR SEQ ID NO:30:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:30:

```
   Thr Lys Ala Lys Ala Arg Val Val Gln Arg Glu Lys Ala Ala
   1               5                  10
```

(2) INFORMATION FOR SEQ ID NO:31:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:31:

```
   Thr Lys Ala Lys Arg Arg Val Val Glu Arg Glu Lys Arg Ala
```

```
                    1               5                    10
```

(2) INFORMATION FOR SEQ ID NO:32:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:32:

```
    Thr Arg Ala Lys Arg Arg Val Val Glu Arg Glu Lys Arg Ala
    1               5                    10
```

AIDS THERAPY AND VACCINE

This application is a continuation, of application Ser. No. 07/766,366, filed Sep. 25, 1991, now abandoned.

FIELD OF THE INVENTION

The present invention relates to AIDS therapies, vaccines and diagnostics.

As used herein, the various titles, and other such headings are intended for guidance, and should not be construed as limiting on the present invention.

PRIOR ART

History

Since its identification in the early 1980's, the cure or prevention of AIDS (Acquired Immune Deficiency Syndrome) has provided a unique target towards which a large number of groups have been working, owing to both its sociological and epidemiological implications. For a while, there was some considerable dispute as to the cause of AIDS and, indeed, opinion is still divided.

Early Theories

Very early on, there was some speculation that AIDS may be a physiological disorder very similar to graft versus host disease (GVHD), an immune disorder resulting from the introduction of foreign immune-competent cells to the victim and characterized by: massive proliferation of blood cells associated with the immune system; loss both of immune responsiveness and self tolerance; and other conditions, such as thymus degeneration and splenomegaly. However, as it became increasingly clear that a virus (HIV—Human Immunodeficiency Virus) was responsible, this theory was necessarily discounted and the search for a treatment or vaccine began.

The Difficulties

The efforts of the various groups involved in the search have been repeatedly frustrated by both the morphology and the metabolic nature of the virus. Thus, potential vaccines and treatments have foundered because of the inherent variability of the virus coat proteins and also because the virus is a member of the group of retroviruses.

The Retrovirus

Most viruses reproduce by infecting a living host cell and then hijacking its metabolic machinery in order to reproduce. When enough new viruses have been created, the cell bursts, and the new viruses are released. The cycle then starts again. Retroviruses take this system one step further and actively incorporate their genetic material into the genetic material of the cell, after reverse engineering their genetic material (in this instance, RNA) into host-type genetic material (DNA).

Thus, it is difficult to detect infected cells unless they are actively producing virus, and latency in HIV, in common with other lentiviral infections, is prolonged, that is, active production of virus may not happen for some time. This seriously hampers, although it does not preclude, research into treatments.

Anti-HIV Drugs

Even AZT (3'-azido-3'-deoxythymidine) cannot cure a patient of HIV-induced AIDS, but can only prevent the spread of the virus within the body by interfering with the process of reverse transcription of viral genetic material into host genetic material. In addition, clinical trials with AZT have shown that relief from the disease is only temporary, and that patients treated with AZT cannot necessarily expect to enjoy a longer life than those receiving no therapy.

Combinations of AZT with other drugs, such as acyclovir, may be of use in AIDS therapy. DDC (dideoxycytidine) may also prove useful but, as DDC acts in a manner similar to AZT, only with lower toxic side effects, it is unlikely to provide the answer to HIV infection.

Vaccines

The alternative to drug treatment is a vaccine to prevent HIV infection or AIDS induced by HIV infection. Vaccines can be either active or passive. An active vaccine causes the body to produce antibodies (an "immune response") against an attacking organism, for example, the AIDS virus (HIV). A passive vaccine will generally consist of pre-produced antibodies, such as from a mouse, rabbit or monoclonal antibody-producing cell line, which can recognize and attack the virus, without the patient's body having to do anything, i.e. it does not have to produce an immune response.

Vaccine Approaches

There are various ways in which to produce a vaccine. The classic vaccine is achieved by injecting the patient with a preparation of killed or seriously weakened (attenuated) virus. The problem with this approach is the potentially catastrophic result if, for some reason, the virus "catched" and the patient actually develops AIDS. Nevertheless, this approach has been investigated, but with only limited success. The immunity raised was sufficient only to provide protection against individual isolates of the virus, but not to HIV from just any source. This is primarily because the coat proteins on the surface of the virus particle are inherently variable and can even vary between one infected person and another. Thus, this approach is unsatisfactory, first because the patient is at risk of developing AIDS, but mainly because whole virus vaccines, in this case, do not necessarily guarantee protection.

Research into HIV Epidemiology

For these reasons, it was desirable to establish how the virus interacted with the human cell, to see whether this provided any explanation for how the virus caused immune deficiency. It was rapidly established that the CD4 protein played a significant role in binding of HIV1 and HIV2 virus to the cell (see, for example, Dalgleish et al, Nature (1984), 312, 763–766). The CD4 protein is characteristically present on a particular subset of white blood cells known as T helper lymphocytes, although the marker is also present on other cell types, such as macrophages, and is known to be present in the brain. Although there have been reports of infection in cell types lacking CD4, such infection has always been induced in the laboratory, and natural infection appears to be overwhelmingly limited to CD4+ cell types.

CD4

The CD4 protein has now been extensively characterized and investigated in mature, or memory, T lymphocytes. It forms part of a membrane complex, CD4T3Ti, which includes the T cell receptor (TCR-Ti), and which is responsible for recognizing MHCII (Major Histocompatibility Complex antigen type II) present on the surface membrane of antigen presenting cells (APC). The interaction between CD4T3Ti and MHC is important in determining whether the T cell is activated by the presence of a foreign antigen. Activation of these antigen-responsive subsets of T cells then leads to their proliferation, and most of these T cells then provide help for the relevant B cells, so that they proliferate and produce antibody against the antigen.

CD4 Anchors MHCII

CD4 does not play a part in recognition of the foreign antigen associated with MHCII, but rather recognizes a portion of the MHCII molecule which is invariant. This interaction anchors the TCR and HMCII molecules in close proximity, so that they may interact. If the interaction is such as to constitute a positive stimulus, then the T cell will be activated.

Structure of CD4

The primary sequence of CD4 shows it to be complex molecule belonging to the immunoglobulin gene superfamily. Some parts of the CD4 molecule resemble antibody molecule V regions, while other parts are essentially unique to the species from which the CD4 is derived (Maddon et al, Cell (1985), 42, 93–104; Clark et al., PNAS (1987) 84, 1649–1653).

CD4 and GP120

A significant interaction between CD4 and the virus is the recognition of the viral coat proteins, gp120, by the CD4 molecule. The gp120 molecule is formed by cleavage from the larger envelope gp160 protein, a smaller gp41 being formed at the same time. Formation of gp120 and gp41 occurs inside the cell, and the two proteins are expressed on the cell surface prior to, and during, the phase in viral replication where the mature virus is budding from the cell membrane. After intracellular proteolytic cleavage occurs, to produce gp120 and gp41, gp120 remains non-covalently associated with the transmembrance gp41. This surface location of the envelope proteins has made them principal targets for vaccines and immunotherapy.

Functional Importance of GP120

It is known that gp120 can directly interfere with CD4+T cell function. One explanation suggested for the immunosuppressive effects of gp120, both in vitro and in vivo, is that high affinity, CD4-gp120 binding prevents antigen-specific MHCII-dependent T cell proliferation, by blocking CD4/MHCII interaction. However, extrapolation to the known immune deficiency, caused by HIV infection in vivo, is not consistent with the observation that deletion of antigen-specific memory T cell responses occurs early in infection, and is apparently irreversible. It is doubtful that any cytotoxic effects of gp120 can explain the marked preferential deletion of "memory" T cell responses, while other T cell responses remain intact.

Attempts have also been made to link HIV infection directly with decline in CD4+T cell number, but the mechanism of CD4+T cell loss, as distinct from loss of T cell function, seems unlikely to be due to a direct viral cytotoxic effect. Other acute cytodestructive mechanisms, such as the cytolytic elimination by CD4+T cells of other CD4+T cells which are expressing or binding gp120, seem unlikely to account for the chronic progressive decline in CD4+T cell numbers.

Differences between Effects of GP120 and whole Virus

Antigen specific memory T cell proliferation is affected by gp120 and by whole virus differently. Whereas gp120 reversibly but immediately suppresses T cell proliferation in response to antigen, there is no equivalent immune suppressive effect produced by the whole virus. The initial proliferative response, as a result of exposure of antigen-specific T cells to antigen presenting cells (APC) pretreated with antigen and HIV-1, is intact. However, the same antigen specific proliferative response is no longer recoverable upon subsequent cycles of antigen stimulation; the effect is due to delayed deletion or to inactivation of the antigen responsive T cells.

Recent Research

Gp120 is a highly variable molecule, and is not susceptible to crystallisation. Many isolates have been sequenced and show very limited conservation of sequence. Some sites on the molecule bear slight sequence similarity to sites on MHC molecules. One conserved region constitutes the CD4 binding site and has been identified. Based on this information, Habeshaw and Daigleish (Journal of AIDS (1989) 2, 457–468) suggested that the gp120 molecule might interfere with T cell antigen recognition, interfering with the interaction between the TCR and MHCII. However, the mechanism of any such interference was not clear, and provided no assistance in the development of a treatment or vaccine for AIDS, and the authors suggested the use of an antiidiotype vaccine based on antibodies to the CD4 binding site of gp120. Difficulties with such an approach exist, as it has proved difficult to define the CD4 binding site for gp120 and MHCII. Attempts to distinguish between those binding sites on gp120 and on MHCII which recognize CD4 also remain unresolved. Thus, Clayton et al. (Nature (1989), 339, p548 et seq.) demonstrated that mutations in the CD4 molecule which affect gp120 binding also affect MHCII binding, but that mutations which affect MHCII binding do not necessarily affect gp120 binding. Accordingly, it would appear that the gp120 binding site forms a specific subset of the MHCII binding site on CD4, and that this unmodified site is accordingly unsuitable for the generation of a vaccine.

Antiidiotype Vaccines

An alternative approach to generating a vaccine against particular pathological viruses is disclosed by, for example, Kennedy et al. (EP-A-0110706) for use, for example, against hepatitis B virus (HBV). Essentially, the virus is injected into an animal in an immunizing amount so as to generate enough antibodies to use as a vaccine. The antibodies isolated from the animal are capable of recognizing the virus, and are 'first generation' antibodies (Ab-1). These Ab-1 antibodies can then be injected into another animal to produce a second generation of antibodies (Ab-2) which recognizes the first generation, and which also mimics a part of the virus surface. The effect of this is to produce something which "looks" like the surface of the virus, and against which an immune response can be raised, but which does not carry any of the hazards implicit in using killed or attenuated virus. Thus, the Ab-2 antibodies can be used as a vaccine. When injected into a patient, a third generation of antibodies (Ab-3) will be generated against the Ab-2 antibodies. Since the Ab-2 antibodies are mimics of the virus antigen, the Ab-3 antibodies can neutralize the virus. This approach has the advantage that patients are not exposed to the whole virus, but cannot be applied to HIV, since the neutralization antigens are too variable.

However, EP-A-287226 discloses a variation on an antiidiotype vaccine, based on the gp120 binding site on CD4. The antiidiotype vaccine disclosed in EP-A-287226 is based on the principle that the CD4 binding site on gp120 is perfectly conserved. Thus, a vaccine comprising antibodies (Ab-1) which bind the gp120 binding site on CD4 is administered to the patient, who will then generate antibodies (Ab-2) against these antibodies (the so called antiidiotype response). These second (Ab-2) antibodies will bind to the CD4 binding site on gp120 and coat the surface of the HIV virus preventing the virus from infecting other cells.

Such a vaccine would be of little use in advanced AIDS, although a corresponding passive vaccine may be of use, as the patient has lost the ability to respond to new antigens. Further, in advanced cases, it is likely that, even if such a vaccine were to work, the patient would remain immune deficient.

Mechanism of the Immune Response

The immune response relies on antigen presentation by the MHCI and MHCII molecules. MHCI is responsible for presenting antigens which are derived from within the cell, and is present on all cells. MHCII is responsible for presenting antigens of extracellular origin, and its expression is essentially limited to cells of the immune system, such as B cells, dendritic cells and phagocytes.

MHCI and MHCII belong to the so-called immunoglobulin (Ig) superfamily, and have domains of their molecules which are closely similar to the constant (C) domains found on antibodies. T cell receptors also belong to this family, and possess both the variable (V) and constant regions typical of antibodies.

As has been stated above, MHCI and MHCII are responsible for presenting antigens. In so doing, linear peptide sequences from processed foreign antigens locate in the characteristic cleft of the MHC molecule. This cleft is formed between two α-helices supported on a β-pleated sheet. CD4 anchors an invariant region outside of the cleft, whilst the TCR recognizes an antigen in association with the cleft. If an antigenic peptide in the cleft interacts with the TCR, the T cell becomes activated.

Although MHCI comprises one polypeptide chain (always found in association with a blood protein $\beta_2$m) while MHCII comprises two polypeptide chains (the α and β chains), their structures are extremely similar. It is not possible to be absolutely certain of the 3-D structure of MHCII, since it has not so far been possible to crystallize MHCII. Nevertheless, MHCII and MHCI share a considerable degree of homology, and the MHCI α chain has been crystallized. Crystallographic analysis has allowed the structure to be determined with certainty. Brown et al. (Nature (1988), 232, 845–850) provide a hypothetical model for MHCII based on the established model of MHCI, and also provide additional sequence data.

Versatility of MHC Molecules

It is known that invading organisms can generate coat, or other, antigens which are capable of evading the neutralizing responses of the immune system. This is possible either by mimicking self antigens, or by mimicking the MHCII/I molecules, or by developing structures which are difficult to process or which do not bind the MHC molecules. Evolutionary pressure of this type has forced the MHC component of the immune system to develop as a highly polymorphic and polygenic gene family with a large number of alleles. Humans possess six pairs of alleles for each of the MHC molecule types (c.f. Nagy et al., Immunology Today (1989) 10, 132–138)

Thus, MHC molecules form several different classes—HLA A, B or C (class I) and HLA DP, DQ or DR (class II), each class differing in the structure of its α or β chain. In any one person, the exact constitution of the α and β chains is inherited from the two parents. Recombination of the paternal and maternal characteristics can occur in the individual, making all individuals essentially unique in their class I and class II fingerprint.

Alloepitopes

Differences in the MHC alpha and beta chain structures between individuals only affect those regions of the molecule interacting with the T cell receptor. These regions are alloepitopes. The other regions of the MHC molecules (responsible for binding to cell membranes and to receptors, such as CD4 and CD8) do not vary between individuals, but do vary between species. The alloepitopes are responsible for presenting antigen to T cells and, because there are many allelic forms of the presentation site, ensure that no two individuals ever respond in exactly the same way to any given antigen.

Because they present the antigen, the MHC molecules also determine which T cell receptors (TCRs) will react with them, and this is dependent on the variable regions of the TCR α and β chains, $V_\alpha$ and $V_\beta$. As there is no evolutionary pressure on TCRs not to recognize a foreign MHC, there are large numbers of T cells in any individual which can, and do, recognize the alloepitopic regions of another individual's MHC.

On the other hand, TCRs will not trigger proliferation or activation of the T cell unless the self MHC contains a foreign antigenic peptide presented in the antigen-presenting cleft (T cell restriction). The TCR, which also shares homologies with the immunoglobulin superfamily, recognizes the shape of the MHC surface. However, foreign MHC can trigger proliferation, even in the absence of antigen, because the alloepitopic surface it presents to the TCR is, somehow, seen by most T cells as self MHC presenting a foreign antigen.

During gestation, thymus ontogeny (development of T cell populations and clones within the thymus) results in a T cell population being generated which is restricted to the types of MHCII molecule presented by the host cells. Clones which do not recognize host MHC, or which recognize host MHC too strongly, are deleted.

Graft versus Host Disease

As has been described, problems arise on the introduction of foreign immunocompetent cells expressing alloepitopic forms of MHC. The resulting disease, when foreign cells are injected into a recipient, is characterized by a general failure of immunity termed "Graft Versus Host Disease" (GVHD). Because of the presence of foreign MHC, the immune system loses the ability to mount a coordinated response to new antigens; reacts to its own self antigens; and loses the memory of responses to foreign antigens. This disorder can ultimately lead to the death of the recipient of foreign cells, such as by intercurrent infection, and immune destruction of vital organs such as the skin, liver and kidney.

The prerequisites for development of GVHD are: 1. presence of immunocompetent cells in the donor inoculum; 2. inability of the recipient to reject the donor cells; and, 3. the existence of a genetic difference between the MHC molecules of host and donor. The resulting GVHD exhibits the following features: 1. hepatosplenomegaly and lymphadenopathy; 2. production of autoantibodies; 3. glomerulonephritis; 4. defective cellular and humoral immune responses; and 5. hypergammaglobulinaemia.

The primary cause of GVHD is excessive activation of T cells, with proliferation of both the donor and recipient cells, although the numbers of recipient cells activated are always greater than the size of the donor inoculum. When a recipient T cell comes into contact with an alloepitopic form of MHCII then, even though it may be antigen specific, it will, in the majority of cases, become activated. For example, Ashwell et al. (Journal of Immunology (1986) 136, page 389) demonstrated that, of 62 cytochrome C specific T cells, 60% were alloreactive, in other words, they became activated in the presence of foreign MHC from the same species, even when the specific antigen cytochrome C was not present.

Alloreactivity in GVHD

The phenomenon of alloreactivity has been extensively studied, and it has been found possible to abrogate GVHD in newborn mice by inoculation of the mother with cells bearing the foreign MHC during her pregnancy. Where the mother is immunized with paternal cells, then the resulting offspring exhibit tolerance to paternal cells, even when these are injected in large numbers. The effect is caused through passing of maternal antibodies through the placenta to the foetus, an event which is known to have a direct effect on the ontogeny of the T cell population.

The effect of the maternal antibodies is not entirely understood, but appears to be the result both of a specific positive selection and a non-specific suppression of a T cell response to paternal cells in the neonate. Thus, it is possible to use a T cell population from the protected offspring of immunized mothers to suppress T cell responses to the immunizing cells in a mouse of another strain. Because of the similarity of TCR used for T cell recognition of allogeneic MHC, the suppressive effects of maternal immunization also extend to decreasing T cell responses to unrelated histocompatibility antigens (c.f. DeGiorgi et al., (Journal of Immunogenetics (1990) 17, 77–88)) when tested by in vitro assay of T cell responses.

The proliferation of T cells in response to alloepitopic forms of MHC is discussed by Termijtelen (Human Immunology (1990), 28, 1–10). Various possibilities for allorecognition are proposed, bearing on the molecular structures which influence recognition of foreign MHC, whether or not antigen is presented by the antigen-presenting cleft. An alloepitopic MHC shows differences both in the shape of the peptide binding groove, and in the surface amino acid residues which interact with the T cell receptor. Alloepitopic responses due to MHC polymorphisms may therefore be due to peptide binding, to "mimicry" of peptide by MHC, or to direct interaction of MHC with TCR. For example, the majority of alloepitope specific amino acid substitutions in tamarind monkey MHCI are located in the antigen binding cleft (Watkins et al., Journal of Immunology (1990), 144, 1136–1143) In another study (Rothbard et at., Cell (1988), 52, 515–523), it was found that a ragweed peptide containing a sequence mimicking MHCII DR was able to stimulate T cells reactive to that particular DR sequence.

HIV and Alloreactivity

Work based on analysis of the whole virus and gp120 alone has demonstrated that APCs infected, or pulsed, with HIV are capable of selectively deleting antigen-specific T cell responses. Clerici et al. (Journal of Immunology (1990) 144, 3266–3271) demonstrated that HIV$^+$ patients who had lost the T cell response to the 'flu virus could, in certain circumstances, regenerate a response to 'flu by co-presentation of a 'flu antigen with a different MHCII molecule. This demonstrates that the capacity to respond to an alloepitope is much less affected by HIV than the more specific and subtle response to a specific antigenic peptide.

Gp120 alone is capable of suppressing T cell activation in the absence of any viral cofactors. This is a direct effect of gp120 binding to CD4 and, which blocks CD4 MHCII interaction and prevents access of the antigen binding face of MHC to the T cell receptor, thereby producing a broad, non-specific suppression of all T cell responses dependent upon MHCII.

GP120 as an antigen

T cell response to HIV gp120 as an antigen is restricted to relatively few immunodominant epitopes. The capacity of T cells to respond to gp120 which has been processed and presented as peptides is determined by the variety and number of T cells in the naive repertoire capable of responding to the presented peptides.

However, since gp120 derived peptides which resemble self peptides elicit no response, the degree of reactivity obtained depends upon the overall similarities between the amino acid sequences of gp120, and various self peptides such as MHC. In general, when self mimicking peptides are presented by syngeneic MHC II or class I, no response occurs. Restricted T cell responses occur to peptides representative of divergence (polymorphism) between self derived, and allo-derived MHC peptides. If gp120 resembled self MHC sequences, a restricted T cell response can be predicted where similarities between gp120 and MHC failed to elicit a T cell response, resulting in T cell tolerance of much of the gp120 molecule.

Analysis of naive T cell responses to synthetic peptides representative of gp120 has revealed an extensive T cell repertoire which identifies about 20 T cell epitopes in the molecule. Significant areas, to which little T cell reactivity is seen, include the area AA 383–453, which forms the CD4 binding site, although responses to AA 458–503 are obtainable. The lack of response to the CD4 binding site is likely to be indicative of conservation of peptide structure (self structure) in this site.

Thus, the available avenues of research into AIDS have yielded much information, but leaving the basic problem of the treatment or prevention of AIDS induced by HIV unresolved.

OBJECTS OF THE INVENTION

It is an object of the present invention to provide a vaccine for the treatment or prophylaxis of AIDS induced by HIV infection.

It is a further object of the invention to provide a vaccine for the treatment or prophylaxis of AIDS induced by HIV infection and which can also restore immunological competence to the patient.

It is a further object of the invention to provide a vaccine for the treatment or prophylaxis of AIDS induced by HIV infection and which can also restore immunological competence to the patient, even in the presence of continued infection with HIV.

It is a further object of the present invention to provide drugs for the treatment or prophylaxis of AIDS induced by HIV infection.

It is a further object of the invention to provide means for the identification of individuals who will not be susceptible the pathology of AIDS, even in the presence of HIV infection.

Other aims and objects of the invention will become apparent in the following description.

SUMMARY OF THE INVENTION

The invention provides a substance which either: a) recognizes an alloepitope of HIV gp160 or one or more products thereof, or b) recognizes CD4+T cell receptors recognizing an alloepitope of HIV gp160 or one or more products thereof, the alloepitope being capable of stimulating proliferation of at least one CD4+T cell clone in a person susceptible to HIV-induced AIDS.

BRIEF DESCRIPTION OF THE DRAWINGS

FIG. 5 also shows a sulfated sugar polymer capable of interacting with the specified residues.

DETAILED DESCRIPTION OF THE INVENTION

Definitions

Figure 1:
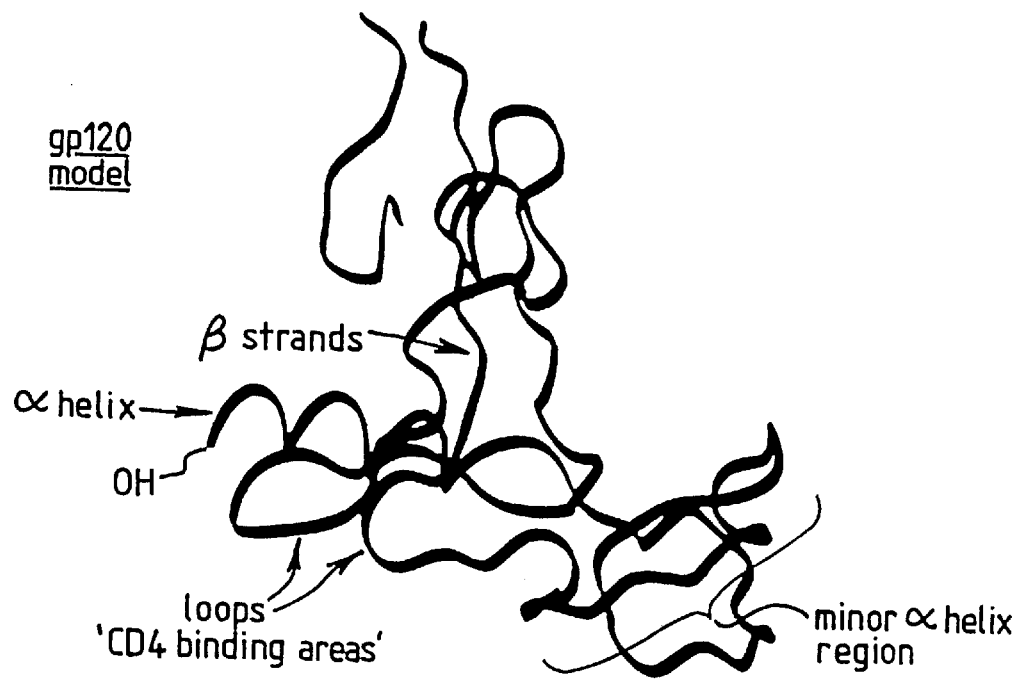
FIG. 1 is a diagrammatic representation of the structure of the gp120 C-terminus and the HLA-A2 $\alpha_2$ chain.
Figure 1:
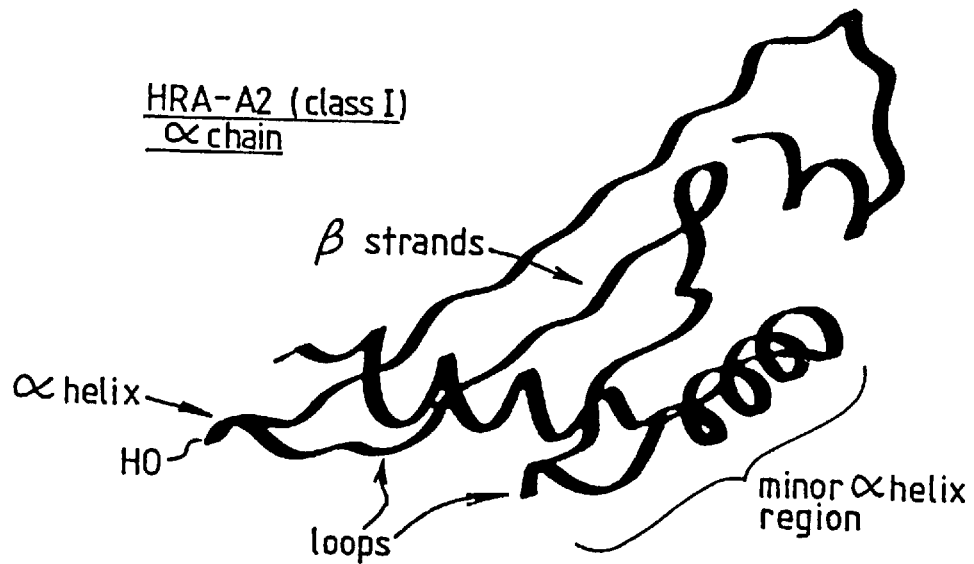

The term 'recognize' is used to indicate that a degree of association or binding occurs when the substance and gp160 alloepitope or T cell receptor are brought together.

The term 'alloepitope' denotes that feature associated with gp160, or one or more products thereof, when presented on a cell membrane, which stimulates proliferation of at least one CD4+T cell clone in a CD4+T cell proliferation assay. The amount of T cell stimulation may vary according to the viral isolate, and it is anticipated that no one alloepitope will give rise to an alloresponse in each and every sample of the population. However, when an alloepitopic effect is observed, it will usually be the case that at least one, and usually a plurality, of clones is stimulated, and that the effect will be observable in a majority of samples taken from a cross-section of the population.

The term 'gp160, or one or more products thereof' is used herein to denote the location of the alloepitope. As will become apparent from the following description, it has now been established that the alloepitope is associated with the HIV gp160 gene product, but it is not known whether the alloepitope responsible for AIDS is associated with gp160 per se, or whether it is associated with the cleavage products of gp160 (gp120 and/or gp41) or even any of gp160, gp120 and gp41 in association with a host molecule, such as MHCI or II, or a part of the host membrane. In addition, the alloepitope may be associated only with an expression product of the HIV gp160 gene, but only when it is in association with the membrane of a host cell. Our experiments indicate that the alloepitopic effect may possibly be primarily associated with the major α-helix of gp120 (see below). In any event, the term 'gp160, or one or more products thereof' encompasses all of the above possibilities, to the extent that it covers that moiety which comprises the alloepitope.

The substances of the invention may, for example, be natural substances, such as antibodies, or synthetic substances, such as engineered proteins, peptides or small organic molecules, or a combination thereof. It is believed that the substances of the invention do not occur naturally, primarily because the alloepitope exerts its effect by mimicking an important self protein and, as has been described above, the body does not naturally produce an immune response against self proteins. Accordingly, the substances of the invention are not naturally occurring, but are made available by the present invention. Thus, the invention provides such substances, as well as methods for generating such substances, both in vivo and in vitro.

In general, it is preferred that the substances of the invention do not recognize CD4+T cell receptors which do not recognize said alloepitope, as this may, in certain circumstances, be too broad, but there may be various applications for the invention where a limited recognition of T cells not recognizing the alloepitope is acceptable. This may especially be the case for immune therapy (see below), where it is preferable to ensure all alloepitope-recognizing clones are deleted, and a margin of error is useful.

The Discovery

The essential fact is that, in individuals susceptible to HIV-induced AIDS, a sub-population of CD4+T cells is alloresponsive to gp160 when expressed on a cell membrane, and these T cells will proliferate in a similar manner as though they were acting alloresponsively to foreign MHCII. Such T cells may be said to be alloresponsive to gp160. The substances of the invention, therefore, either recognize that portion of gp160 responsible, i.e. the alloepitope, or recognize those T cell receptors which are alloresponsive to gp160.

The alloepitope has been found to be associated with membrane-expressed gp160, but may be specifically associated with gp120 alone, or with gp120 and gp41 together, or with the uncleaved version of gp160, any of which may also need to be associated further with a membrane component to evince the alloepitope. Association with a part or all of MHCII, for example, may be required. It is particularly likely that the alloepitope is associated with the major α-helix of gp120 when associated with the cell membrane, especially of an antigen presenting cell, although presentation by MHC does not appear to be required. Association of the α-helix peptide with MHCI and MHCII is likely, even in this circumstance.

Potential Applications

The invention envisages the use of the substances defined above in a number of fields which include, but are not necessarily limited to, the following:

i) Vaccines against HIV-induced AIDS, the vaccines being either active or passive;

ii) Immunotherapy for the treatment or prophylaxis of HIV-induced AIDS;

iii) Diagnostic tests and methods to identify persons susceptible to or suffering from HIV-induced AIDS;

iv) Preparations or pharmaceuticals for the treatment or prophylaxis of HIV-induced AIDS; and v) Assays for potential anti-HIV-induced AIDS therapies.

The Alloepitope on HIV—the causative Agent of GVHD

We have now discovered that the gp120 molecule is capable, when expressed on, or associated with, the surface of a host cell, of stimulating CD4+T cells in the manner of an alloepitope, thereby giving rise to a form of GVHD.

Thus, despite AIDS being caused by a viral infection, the pathology of the disease results from a coat protein of the virus mimicking or interfering with MHC and inducing disease resembling graft versus host disease.

More specifically, when expressed on, or associated with, the cell membrane, gp160, or gp120 in association with gp41, mimics foreign MHC. That portion, recognizable by some CD4+T cells, is the alloepitope, and it mimics allogeneic MHCI or MHCII (an intra-species variant of MHCI and II), although it seems most likely that it is the mimicry of MHCII which gives rise to the characteristic pathogenesis of AIDS. This mimicry leads to the production of disease similar to GVHD. The disease also involves suppression or deletion of immune responses restricted to or dependent upon syngeneic MHCII. The effect of gp160 may also require, or be enhanced by, an association with an MHCII monomer.

In molecular terms, membrane-expressed gp120/gp41 binds CD4 and interacts with the T cell receptor in such a way that it appears to be a foreign or allogenic MHCII molecule. In common with allogeneic MHCII, gp120 in association with gp41 on the cell membrane will stimulate a fraction (in the case of HIV-induced AIDS, probably a very small fraction) of the CD4+T cells, leading to the GVHD-like AIDS syndrome. Since there is no mechanism which physiologically prevents T cells from interacting with allogeneic MHC, any mimicry of an alloepitope will activate at least some T cells in the great majority of normal individuals. Most people, therefore, will prove susceptible to the development of AIDS following HIV infection. The B cells which are helped by the T cells to produce antibodies, do so according to T cell stimulation. As T cell stimulation through the effect of an alloepitope is essentially random there is, accordingly, only a small random chance of B cell antibody production affecting the HIV infection. Thus, HIV infection can continue and a condition similar to GVHD may develop.

Gp160 and Gp120—Similarity to MHCII

As used herein gp120 and gp160 are interchangeable, as it is not certain whether the alloepitope is associated with gp160, or with gp120 possibly in combination with gp41, or by some combination of these. The HIV glycoprotein gp120, and the associated gp41 fragment, probably act in the form of an alloepitope when expressed upon the membrane of infected cells.

While it is apparent that gp120 is an essential part of the HIV associated allogeneic effect, it may not be the effect of gp120 alone, but possibly gp160 or, more probably, an association of gp120 and gp41 on a cellular membrane. It is also possible that the alloepitopic structure may be enhanced by the presence of MHCI or MHCII, either directly on the same cellular membrane as gp120, or in the case where cells interact by contact, but it is apparent that neither MHCI nor MHCII molecules are essential to the effect, as experiments have been performed where the allogeneic effect is observed in the absence of either MHCI or MHCII.

In addition, while the allogeneic effect of HIV may be principally limited to gp160 expression on antigen presenting cells, the effect may also be produced by the expression of gp120 (or gp160) by other cell types, such as HIV-infected CD4+T cells, in vitro and in vivo.

Mode of Expression of Cell Surface

It is known that gp160 is expressed on the surface of infected cells. It is also known that gp160 expresses the heat-shock protein motif. Proteins bearing this motif tend to accumulate in lysosomal and endocytic compartments, and hence gp160 produced by the virus is likely to be expressed within lysosomal compartments in membrane-associated form.

Both MHCI and MHCII recycle through the endocytic pathway, which is involved in antigen processing and presentation. It is here that they are exposed to both exogenous and endogenous peptides. The peptide/MHC complex is then presented on the cell surface. It is likely that the intracellular pathways of gp160 in virus-infected cells mimic those of MHCI and MHCII molecules, with a cellular protease cleaving the gp160 molecule after its expression upon the endocytotic vesicular membrane.

Thus, gp160 presented at the endocytotic membrane surface is available for cleavage by cellular proteases into gp120 and gp41 fragments. Gp120 may then be expressed together with $gp^41$ on the surface of infected cells, such as CD4+T cells and antigen-presenting cells. It seems likely that gp120 and gp41 together, when presented on the external cell membrane, sufficiently resemble the MHCII or MHCI molecule to be able to stimulate alloreactive CD4+T cells. This effect may possibly be enhanced either by forming a complex with a further gp120/gp41 dimer, or by forming complex associations with other membrane molecules such as MHCI or MHCII, or with proteins such as $\beta_2$ microglobulin.

Previous Observations

This also explains the observations of Schols (Abstract No. 3573, 6th International Conference on AIDS, San Francisco, Calif., USA, 20th to 24th June 1990), who demonstrated that antibodies against MHCII molecules could be shown to bind to cell membranes on which HIV virions were budding. Despite the fact that the T cell line employed expresses HLA DP, DQ, and DR when activated, the increased sensitivity due to virus infection was only detected by monoclonal antibodies reactive with DR. In accordance with the present invention, this phenomenon can be explained by postulating that the virus envelope glycoprotein exhibits regions resembling HLA DR (MHCII) epitopes when expressed by budding virus (i.e. as gp120/gp41), but not after disassociation of the gp120 moiety, when mature virus is shed. Thus, it is likely that the HIV alloepitope is a functional epitope of HLA DR.

Possible Alternative for Allostimulatory Effect

An alternative explanation for the allostimulatory effect of HIV is that gp120, possibly in combination with gp41, serves to cross-link or enhance binding of the T cell receptor to MHCII, serving to spuriously stimulate T cells.

However, our results (see Example 4 below) clearly indicate that it is not necessary for syngeneic MHCII to be present in order to stimulate alloreactive T cells. Target cells, such as CHO cells, which express gp160 and MHCI, but not MHCII, were shown to stimulate human T cells, most of which were CD4+T cells which normally interact only with human MHCII. CHO cells atone do not stimulate an equivalent CD4+T cell population, and no stimulation is observed with a preparation of gp120. Thus, gp160 expressed on the membrane of CHO cells as gp120/gp41 probably interacts directly with the T cell receptor and CD4 in such a way as to stimulate an alloreactive T cell population.

Whatever the mechanism, in individuals susceptible to HIV-induced AIDS, the gp160 alloepitope gives rise to a disease condition similar to GVHD.

Effect of Alloepitopic Stimulation

Initial selection of T cells during gestation (thymic ontogeny), selects those T cell receptors which interact strongly with self MHC, but also which do not subsequently react to self MHC by proliferation in the absence of antigen. There is no mechanism to delete T cells which will react to foreign MHC by proliferation in the absence of antigen. In the absence of such elimination, a large proportion of T cells will have receptors which will interact with and which will be stimulated by foreign or allogeneic MHC, if that MHC sufficiently resembles host MHC.

As there is no basis for natural selection against foreign or allogeneic MHC, both foreign MHC and substances sufficiently resembling self MHC are able to artificially stimulate certain sub-populations of the host T cell population, which leads to GVHD.

However, gp120, while sharing a degree of tertiary structural homology with MHCII, is not sufficiently similar to MHCII to stimulate more than a small population of CD4+T cells, possibly as low as 2%, and quite possibly even lower. The overall allogeneic effect is further likely to be enhanced by the very high affinity of gp120 for the class II receptor, CD4, so that very little similarity between gp160 and MHC is required outside the CD4 binding region.

Further, when alloreactive T cells are activated by the alloepitope, a proportion will become restricted to the alloepitope, and will be preferentially stimulated by the alloepitope, rather than by syngeneic MHC in association with specific antigen. This effect may be so marked that the cells eventually lose the ability to recognize self MHC, and is likely to be markedly enhanced by the fact that gp120 is estimated to bind CD4 from 1,000 to 10,000 times more strongly than does MHCII.

Stimulation of an alloreactive T cell population, in general, leads to chronic immune deficiency with weight loss, runting, and failure to thrive. The cause of this immune failure is the continued presence of alloepitope expressing cells which continue to stimulate T cell production, but against which no coordinated response is raised.

In a normal response, the relevant antigen, in association with MHC, stimulates T cell production in a selective fashion, so that B cells produce antibodies directed against the antigen or invading agent. This results in a reduction of antigen and, accordingly, a reduction of stimulation, so that the system does not become dominated by one clone each of T cells and B cells. However, the HIV alloreactive T cell response is independent of any antigen presentation, and is dependent only on the presence on the cell surface of gp160. This leads to disorganized activation of antibody-producing cells, as well as cytotoxic T cells, as the effect leads to stimulation of random clones.

One of our observations is that stimulation of the production of cytotoxic T cells by the peptide corresponding to the gp120 major α-helix yields cytotoxic cells capable of indiscriminate, or non-specific, killing of antigen presenting cells, regardless of associated antigen. The result is to further reduce the possibility of producing a genuine immune response to other antigens by the indiscriminate removal of the relevant APCs.

Apart from increased susceptibility to infection, the continued proliferation of alloreactive T cells proportionately reduced the capacity to mount immune responses to antigens, especially MHCII-restricted T cell responses, and can lead to the generation of autoreactive antibodies. Hypergammaglobulinaemia, presence of autoantibodies, and renal damage also may result, and are also observed in AIDS.

Effect of Genetic Variation of T Cell Receptor

It is known that the genetic background of inbred mice governs whether or not alloepitopes of MHC, and MHC-mimics, such as MLSa, are recognized. Accordingly, it is also likely that a minority of human individuals will not recognize gp120 as an alloepitope. Such individuals will respond to gp120 as a conventional viral antigen and will probably never develop AIDS, despite being productively infected with the virus. It is almost certainly this mechanism which renders HIV infected chimpanzees immune to AIDS development, even though both the structure of their CD4 molecule and of their MHCI and MHCII antigens is very similar to man's.

Infection without Developing AIDS

Thus, a productive infection of HIV may occur, but AIDS never develops, if the T cells of that person fail to recognize gp120 as an alloepitope. It will be appreciated that there are two phenomena that require consideration: the immune response to HIV as a virus; and the alloepitopic response to gp160. In the majority of HIV seropositive individuals, both antiviral and alloepitopic reactions occur together, resulting both in partial immunity and in AIDS susceptibility. HIV seropositive individuals who lack alloantigenic responses will suffer no disease as a consequence of infection.

Pattern of HIV Infection in the Chimpanzee

Comparison of the MHC of the chimpanzee with that of man (Fan et al., Human Immunology [1989], 26, 107–121) demonstrates that chimpanzee MHC sequences differ in only minor positional and sequence changes from the human form. Both human and chimpanzee T cells interact reciprocally with their respective CD4 and MHCII molecules.

The important differences in reactivity to HIV between human and chimpanzee probably lie in the variable region gene repertoire naturally expressed by the T cells of these species. The lack of alloreactive T cells in the chimpanzee T cell repertoire, when presented with gp120/gp41 on the cell membrane, precludes the development of AIDS in the chimpanzee. Conversely the presence of a mere 1–2% or less, for example, of T cells recognizing gp120 as an alloepitope in man can induce widespread susceptibility to AIDS in the human population. Those individuals lacking an alloreactive T cell component recognizing gp120/gp41 may, thus, develop a productive viral infection, but not AIDS.

People whose T cell receptors do not recognize gp120 as an alloepitope are, therefore, not necessarily immune to infection by HIV, but are immune to HIV-induced AIDS, as AIDS only occurs when the immune system recognizes gp120/gp41 as an alloepitope of MHC.

Elimination of Susceptible T Cell Population

It will be appreciated that AIDS can be treated by the elimination of alloreactive T cell sub-populations, allowing immune competence to regenerate from remaining T cells.

As stated above, the region of the T cell receptor responsible for recognition of the gp120 alloepitope is the domain comprising the Vα and Vβ regions. If a person is susceptible to AIDS, only those T cells having an appropriate Vα and Vβ combination in the T cell receptor will be alloresponsive to gp120. This T cell population is likely to be between 2% and 10% based on our data.

Elimination of this small, alloresponsive T cell population would be unlikely to decrease immune capacity, as it is known that the T cell repertoire is tolerant of widespread clonal deletion, and a full spectrum of immune responsiveness can be maintained by a relatively small T cell population. Even if the alloresponsive population were larger than 10%, the remaining T cell clones would generally be able to diversify to provide a normal, or near normal, complement of protection.

Thus, although T cell clones will have been eliminated, and the overall variation in the T cell repertoire reduced, the individual will no longer be susceptible to AIDS, even though HIV infection may persist.

After such clonal deletion, the remaining T cells will not be alloresponsive to gp120, but are likely to remain alloreactive with other donor MHC types, as not all alloepitopes resemble either each other or the gp120/gp41 alloepitope.

Potential Areas of Diagnosis and Treatment

The alloreactivity of an individual's T cells to gp120/gp41 is indicative of the individual's susceptibility to AIDS. Thus, the present invention allows the identification of people who are refractory to HIV-induced AIDS. Such data is of importance in areas such as vaccine design and epidemiology, and can reduce the cost of AIDS to the community, as the need to treat people who are HIV+ but who will not develop AIDS is reduced. This may also be of benefit to the refractory population, in minimizing contact with anti-HIV therapies which may, in themselves, have undesirable side-effects. Thus, only those who are susceptible to AIDS need be treated.

Tertiary Structure of Gp120

It is with the elucidation of the tertiary structure of gp120 that the problem of AIDS pathogenesis has been solved.

Modelling the structure posed considerable problems. Gp120 is a large, heavily glycosylated molecule which does not crystallize, so its structure cannot be elucidated by X-ray crystallography. Certain regions of the molecule can be analyzed for secondary structure, but this reveals little of note, and has not previously been considered worth pursuing.

The sequence of gp120 is known, but it was not considered that there was any great sequential homology between gp120 and either of the MHC molecular types. However, if molecular modelling is performed on gp120 then, without forcing a fit, and only calculating likely areas of $\alpha$-helical and $\beta$ sheet structure, a surprising degree of structural homology between gp120 and the MHC molecules is found.

Essentially, MHC-like tertiary structure is predicted when important conserved regions are given priority, and theoretical and empirical considerations, such as the Chou and Fasman rules, which are generally available, applied to the known sequences of gp120. The similarity when MHC is considerably enhanced when the surface structures and conserved glycosylation sites in the gp120 molecule are considered.

Similarities between Gp120 and MHC

Gp120 and MHCI and MHCII have very similar $\alpha$-helical regions. One conserved domain of the gp120 molecule exhibits a strong degree of similarity to an MHC major $\alpha$-helix, which constitutes a primary T cell receptor binding site. This observation led, in part, to the present invention.

A strong $\alpha$-helical region of the gp120 molecule has similar sterism to the MHC major $\alpha$-helix, having a similar orientation in relation to overall structure, and particularly in relation to a major $\beta$ domain and the CD4-binding loop. This $\alpha$-helix of gp120 is referred to herein as the, or the major, $\alpha$-helix of gp120. It seems likely that gp41, in association with gp120, serves to form a structure resembling the antigen presenting face of the MHC molecules (see FIG. 1).

Closer analysis of the major $\alpha$-helices yields yet more similarities between gp120 and the MHC antigens. In particular, in the MHC molecules, there is a group of basic residues projecting from one face of the helix. A corresponding group, although not identical to those of MHC, projects from the corresponding face of the gp120 $\alpha$-helix. However, there is another group on the gp120 $\alpha$-helix, on a face rotationally removed from the first, that allows molecular discrimination between the gp120 $\alpha$-helix and those of MHCI or class II.

The first, shared group of residues is known to be important in T cell receptor binding. Given the proximity and generally conserved nature of the second group, not only is this group a particular target for the present invention, but it is also likely to influence T cell receptor binding. This second group is remarkably conserved in all of the isolates of HIV so far analyzed.

Rider

While the alloepitopic effect of HIV is most likely based primarily on the $\alpha$-helical similarities between MHC and gp120, and the relative orientation of these regions to the remainder of the molecule, and while the alloepitopic effect can be observed by the use of the gp120 major $\alpha$-helix alone when associated with the cell membrane, it will be appreciated that the similarity between gp120 and MHC responsible for T cell activation does not necessarily lie solely in the major $\alpha$-helix of gp120. The ability of gp120 to bind to CD4 with high affinity probably also constitutes part of its ability to mimic MHCII, for example.

VACCINE APPLICATIONS

Prevention of HIV-induced AIDS

A primary purpose of the present invention is to provide vaccines to prevent HIV-induced AIDS. Such vaccines may be active or passive and contain a sufficient amount of a substance of the invention to either: stimulate an immune response against the alloepitopic structure of HIV; or act against this component of HIV directly; or stimulate an immune response against those T cell receptors which are alloreactive with the alloepitope of gp160; or act directly against such T cell receptors.

The vaccines of the invention may comprise any suitable substance of the invention, but the present discussion will be limited to antibodies, although it will be understood that the vaccines of the invention are not so limited, and other substances useful in the vaccines are described herein and in more detail below.

Accordingly, the antibodies used in the vaccines of the invention will either: a) recognize an alloepitope of HIV gp120 or one or more products thereof, or b) recognize CD4+T cell receptors recognizing an alloepitope of HIV gp160 or one or more products thereof.

The antibodies of category a) will, when used in vaccines to alleviate immune deficiency caused by HIV infection, either be used in a passive sense against any challenge, or in an active sense so as to generate an immune response to eliminate T cell alloreactivity to HIV gp120/gp41. Those of category b) may be used in active vaccines, or may generally be used in passive vaccines to suppress or eliminate alloreactive T cell clones.

Passive Vaccines

Antibodies recognizing an alloepitope of gp160 (gp120/gp41) should not, where possible, be so general as to also recognize MHCII. Recognition is undesirable for two reasons, the first being the inherent undesirability of antibodies directed to an important self-protein. The second reason is that the ability to recognize other substances than gp160 can only serve to dilute any effect that the antibody might have, by binding something other than gp160.

To avoid this problem, either antibodies having general recognition of gp120/gp41 can be produced and then screened to eliminate MHC reactivity, or specific antibodies with singular reactivity can be produced by, for example, hybridomas. Production of general antibodies by, for example, immunizing animals and separating the desired product, a polyclonal antiserum, is generally undesirable (although still included within the scope of the invention) owing to the uncertainty of the content or specificity of the end-product.

Specific antibodies and antibody conjugates may be produced by monoclonal technology. Such antibodies may be sufficiently specific to be able to recognize the alloepitopic component of all gp160 molecules, or may recognize only one. Antibodies capable of recognizing several forms of gp160 alloepitope may either possess a complementarity determining region (CDR) which reacts with variable affinity with the alloepitopic domains, or may be selected to react against peptides, for example, which exhibit only the common T cell receptor binding features of the various gp$^{160}$ isolates, in which case binding affinity should be consistent.

Antibodies which block the alloepitopic reactivity of a single isolate of gp160 may provide strong protection against the allogeneic activity of individual strains of HIV. It is generally more useful to combine several antibody types in any vaccine, in order to broaden the therapeutic effect.

Preferred vaccines include a range of antibodies of varying specificities as defined above.

Active Vaccines

Active vaccines against the alloepitope will include antibodies directed against alloresponsive T cell receptors, that is, those T cell receptors which recognize gp120/gp41 or gp160 sufficiently for the T cell to be activated by the alloepitope.

Those T cell receptor V region domains which recognize gp160 will resemble antibody V regions to the extent that the V regions of the T cell receptor, in common with the variable regions on antibodies, are responsible for determining the specificity of interaction of the T cell receptor with the target alloepitope. Accordingly, antibodies which recognize the T cell receptor alloepitopic reactive region may exhibit CDRs which cross react with those antibodies used in the passive vaccines. Such antibodies are specifically the AB2β antiidiotypes of the Ab1, the alloepitope specific antibodies.

Raising antibodies which are specific for only those T cell receptors which recognize gp160 can be achieved in a number of ways. One method is to produce gp120/gp41 alloepitope specific antibodies as used in the passive vaccines, and to immunize an animal with the antibodies to produce an Ab2β antiidiotype response. The idiotype/antiidiotype network response, described by Jerne, ensures that an image of the antigen (or in this case alloepitope) is introduced into the immune system, which will thereafter continuously produce Ab2β antibodies which are antigen reactive, even though the antigen is no longer present in the system. These Ab2β antibodies can be used in the sense of an active vaccine of the invention, by inducing an Ab2β antiidiotype response as an immune response against the appropriate alloepitope of HIV.

Alternatively, T cells expressing the alloreactive T cell receptors can be isolated and screened for reactivity to the alloepitopic determinants of gp160. Those T cell receptors which bind gp160 can then be cloned, or used as cell preparations, to generate an antibody response in a suitable animal. Alternatively, the animal may be immunized with whole T cells expressing the relevant T cell receptors, although this is likely to give rise to spurious responses. The resulting antibodies may then be used in the active vaccines of the invention.

Other considerations applicable to the active vaccines of the invention are as defined above for the passive vaccines, such as antibody specificity and range of antibody type.

Virus-Containing Vaccines

Active vaccines may also comprise whole HIV where it is desired to produce a response against a component of the virus other than the alloepitope. Accordingly, there is provided a vaccine against HIV-induced AIDS, comprising an amount of HIV effective to elicit an immune response thereagainst, and a suitable carrier therefor said HIV having no effective gp160 alloepitope or one or more products thereof recognizable as an alloepitope by any host CD4+T cell receptors. The HIV is preferably killed by any conventional means, so as to avoid the risk of non-AIDS inducing infection.

To produce the virus for the vaccine, this can be done by genetically altering a strain of HIV such that the genetic code for said gp160 alloepitope is deleted or mutated, to render said gp160 alloepitope, or one or more products thereof, ineffective to stimulate human CD4+T cell receptors. Such mutation or deletion may comprise only the deletion or mutation of a single base, or deletion of the whole gene, provided that the alloepitope is effectively inactivated. Any conventional method may be used to effect the mutation or deletion, such as site-directed mutagenesis, or transformation with a defective gene.

General Considerations

In general, considerations above, with regard passive and active vaccines, are also appropriate to passive and active vaccines against T cell receptors.

Any of the vaccines provided by the invention may use antiidiotype antibodies, where appropriate, or further antiidiotypic generations. Second generation (Ab3) antiidiotype antibodies may be useful, for example, in providing the active vaccines described hereinbelow with respect to immunotherapy.

Antibodies for use in the vaccines of the invention need not necessarily be entirely natural in origin, that is, for instance, it is possible for useful antibodies to be engineered containing peptide sequences such as those described under 'Peptides,' below.

Antibodies may be engineered using genetic sequences encoding single V regions reactive with the appropriate target epitope (single domain reagents), or using CDRs from antibodies raised in animals, and inserting these in human antibodies to minimize any adverse response to a foreign protein.

One advantage to the production and use of antiidiotype or engineered single domain antibodies is that innate tolerance of self proteins, such as the T cell receptor, or the α-helix of HLA can be overcome. Because gp160 resembles a self-antigen, at least in some respects, it may be difficult to direct immune responses to the appropriate peptide sequence, but this constraint does not apply to immunization using antiidiotype antibodies or engineered antibodies with selected V region domains. Responses can usually be generated to Ig variable regions, even in patients who are HIV seropositive and have AIDS.

Accordingly, engineered antibodies may be of use in antiidiotype vaccines.

It will be appreciated that antibodies for use in accordance with the present invention, whether for diagnostic or therapeutic applications, may be monoclonal or polyclonal as appropriate. Antibody equivalents of these may comprise: the Fab' fragments of the antibodies, such as Fab, Fab', F(ab')$_2$ and Fv; idiotypes; single domain reagents or antibodies engineered therefrom, or from isolated CDR domains, for example. Other suitable modifications and/or agents will be apparent to those skilled in the art.

It will be appreciated that mimotypes of the said antibodies can be used in accordance with the present invention. The term mimotype, as used herein, means a peptide, or peptide derivative, specifically synthesized to bind the paratope of a given antibody. Mimotypes may be prepared according to the methods of Geysen, H. M., et al. (PNAS, [1984], 81, 3998–4002 and PNAS [1985], 82 178–182, incorporated herein by reference in its entirety).

A peptide as defined below under 'Peptides' may be used directly, or may be part of a larger structure, and may, for example, be presented on a carrier for purposes of raising antibodies, although it is envisaged that the gp120 peptide is a sufficiently strong helix former that it will be adequately, or strongly, immunogenic in its own right. A preferred peptide corresponds to a substantial portion or all of the major α-helix of gp120. This peptide can produce the alloepitopic effect in cytotoxic assays, but can be used in tolerising amounts, such as between 0.1 and 200 μg/dose (where the dose is suitably 0.5 ml), especially between 1 and 100 μg/dose and particularly between 10 and 50 μ/dose, in vaccines such that, if HIV infection occurs, the naturally occurring sequence, even if cleaved to closely resemble, or be identical with, the immunising sequence, cannot cause AIDS. A particularly preferred sequence is T K A K R R V V E R E K R (SEQ ID NO. 1) but others are defined below.

When considering the use of the peptides of the invention for raising antibodies and generating immunity, it may well be desirable to produce a range of peptides to help ensure that all HIV isolates are subject to any immunity or assay, for example, and to ensure that the virus cannot defensively mutate to escape the effects of any vaccine.

It will be appreciated that the present invention also extends to a process for the preparation of a vaccine as described, comprising providing an effective amount of a substance as defined, and contacting the substance with a suitable carrier therefor.

Administration of large quantities of non-human antibodies expressing domains which are immunogenic to the patient may well lead to an immune response capable of neutralizing the effect of the vaccine over time, although this is initially unlikely in the circumstance where the patient has already developed AIDS. Circumvention of the problem may be achieved, as suggested above, by CDR (Complementarity Determining Region) grafting, in which an antibody of the relevant specificity is generated in a non-human animal, and the effective region, that is the V region, of the molecule grated into a human antibody molecule at the cDNA level. This is achievable by known techniques.

Active vaccines require considerably lower levels of antibody, or equivalent, than are required in passive vaccines, which need to contain sufficient antibody to directly interact with all target antigens in the patient to be able to prevent productive infection. In an active vaccine, the appropriate immune response generated is continuous and proportional to the body load of the target epitope. An antibody response to the V regions of the administered antibody would induce antibody responses in the manner and specificity of a passive vaccine which would serve to eliminate T cell responsiveness to the alloepitopic determinants of gp120.

Administration of the vaccines and treatments according to the present invention will vary according to the circumstances, taking into account such factors as age, weight and general condition of the patient.

The vaccine may be administered as one self-sufficient dose or as a series of doses over a period of time.

Repetition of dosing either to boost or maintain immunity is also generally desirable at a later time, conveniently about 3 months later, but such booster dosing may be given earlier or at any time during the remainder of the lifetime of the patient, and on as many occasions are necessary.

Pharmaceutical grade saline may be used as carrier for the antibody or antibodies, to provide a simple vaccine. However, as the antiidiotype response to such a formulation for an active vaccine may not be very strong, it may often be preferred to use adjuvants.

Particularly useful adjuvants and carrier proteins for use in accordance with the present invention are keyhold limpet hemocyanin (KLH), muramyl dipeptide and alum preparations. Use of these substances has been found to greatly enhance the Ab-2 response and so vaccines containing such substances form particularly preferred embodiments of the present invention.

In passive vaccines, there is no requirement for an adjuvant. However, where an antiidiotype response is to be generated, then an adjuvant, together with an immune-stimulating quantity of monoclonal antibody (MAb), may be useful.

Adjuvants may be administered together with MAb, in the same or different preparations or separately, at a time different from that of the administration of the vaccine.

Vaccines according to the present invention will usually be administered by a conventional route such as, for example, by injection by the intravascular, intraperitoneal, intramuscular or subcutaneous routes. Other suitable routes may comprise intradermal inoculation or administration via particulate aerosols.

Such vaccines will normally comprise a pharmaceutically acceptable carrier and optionally an adjuvant, substances to render the vaccine isotonic with the body fluids and such flavorings, emulsifiers and other ingredients as may be required.

Such vaccines as described above may be sub-divided for separate administration, whether simultaneously or over a period of time, suitably weeks.

Methods of Antibody and Cell Line Production

Where it is desired to raise antibodies against the T cell receptors, it is preferable to use gp160 alloreactive CD4+T cells, as such cells recognize gp120 and not MHCII as the alloreactive product. Suitable cell lines can be readily produced, as is exemplified herein.

The protocol for obtaining the necessary antibodies may be performed in any suitable animal, such as rodent equine, similar, ungulate or primate species, and antibody-expressing cells harvested and monoclonal hybridomas raised by standard techniques as known in the art.

To generate the necessary classes of T cell, various protocols can be envisaged. For example, syngeneic APCs (antigen presenting cells) and peripheral blood lymphocytes (PBL) can be obtained and isolated by known means. The two classes are then separated. The APCs may then be pulsed with HIV. This results in the HIV being taken up by the APCs, and the resulting envelope glycoprotein of the virus being expressed upon the cell membrane. The HIV infected APCs are then used to stimulate syngeneic or allogeneic T cells. T cells which proliferate are then harvested and further introduced to HIV-pulsed APCs. The cycle is repeated several times to obtain a population of T cells alloresponsive to gp120. Such cells will proliferate to appropriately expressed membrane associated forms of gp120/gp41, and may even be restricted to antigen presentation by gp120/gp41. Restricted T cell clones can be isolated from the initially alloresponsive T cell pool.

To ensure that the gp120-restricted T cells generated above are alloresponsive to gp120, they can be introduced to, for example, rodent cells transfected with DNA coding for gp160 and expressing gp120/gp41 on the membrane. T cells which will proliferate (in a similar method to that described above) are gp120-alloreactive. However such alloreactivity does not indicate restriction solely to the gp120/gp41 alloepitope.

To generate T cells which are gp120/gp41 alloepitope restricted, further selection based on the antigen-specific responsiveness of the gp120/gp41 alloreactive T cell lines generated above, is required. Proliferating T cells obtained by this process will be antigen-specific, and gp120-restricted.

The two classes of T cells obtained by these protocols will either only proliferate in response to membrane expressed gp120 without any requirement for antigen, or will only proliferate in antigen specific manner when exposed to antigen in the presence of gp120, and not in the presence of other MHC alloepitopes.

Accordingly, these two T cell classes are referred to herein as a) gp120-specific and b) antigen-specific, gp120-restricted.

Useful HIV Strains

In the above protocol for preparing gp120-specific and restricted T cells, the HIV used to prepare the cultures should not be able to produce productive infection, as this could seriously hamper the technique. Accordingly, we have prepared an HIV mutant deficient in the reverse transcriptase gene, and which can bind to cells and internalize. Mature virions can only be produced by transfection with a plasmid encoding the mutant virus DNA. The accompanying Example (1) illustrates the means of production of this mutant.

Other HIV reverse transcriptase deficient mutants are described, for example, by T. Folks et al. J. Exp. Med. 164:280; M. Lightfoote et al. (J. Virol. 60:771–775), and H. Gendelman et al. (Virion 160:323–329).

Mutants which have been constructed are illustrated by J. Hansen et al. (EMBO 7:239–243), who describe a mutant prepared by removing the fragment bounded by two Kpnl restriction enzyme sites from the POL gene, using the cloned POL gene, and M. Tisdale et al. (J. Virol. 63:3662–3667) who constructed a similar mutant.

IMMUNOTHERAPEUTIC APPLICATIONS

Treatment of HIV-induced AIDS

The present invention also provides immunotherapy to treat HIV-induced AIDS, either by being directed against the virus or the susceptible T cell clones. Thus, immunotherapy in accordance with the present invention serves either to eliminate those CD4+T cell clones which are alloresponsive to gp120 or gp160, or to act directly against the alloepitope in an infection.

Times for Treatment

Elimination of the alloresponsive clones means that the proliferation of susceptible T cell clones is halted, thereby allowing a reversal of the AIDS condition. Treatment of an HIV-induced AIDS sufferer will eliminate the clones involved in the GVHD-like reaction, leaving only a normal T cell population which is not alloreactive to gp120, and which responds conventionally to environmental antigens.

Methods of Treatment

Immunotherapy may be performed in a manner analogous to vaccination, as described above. The substances which may be used [?] immunotherapy in the invention are as defined above for vaccines. These include active and passive immunotherapy with antibodies, for example. The immunotherapy of the invention will generally be described with reference to antibodies, although not being so limited, other substances as described herein being usable, such as defined under 'Peptides,' hereinbelow. Antibodies which may be useful, for example, can have similar propeptides to those used as vaccines, but may preferably be directed principally towards the T cell receptor or T cell receptor products rather than the alloepitopic structures of gp120/gp41. As described below, the immunotherapeutic agents can involve an analogous range of peptides representative of T cell receptor, as well as peptides derived from gp120 structure.

Immunotherapeutic Vaccines

The immunotherapy of the invention is targeted toward alloresponsive T cell receptors or to HIV. The intention of immunotherapy is not to prevent HIV-induced AIDS (vaccine), but to treat the immune deficiency which results from HIV infection.

Accordingly, both active and passive forms of therapy are envisaged, and both may be employed, although stage of infection, if any, will tend to affect the choice.

Active Immunotherapy

Agents used for active immunotherapy will be used to induce an antibody response against the HIV alleopitope or alloreactive T cells in a patient who has started to progress towards AIDS, or will act directly on the virus or cells. Alternatively, the agents, or vaccines, will serve to bind the alloepitope, or produce a response thereagainst, so as to eliminate virus or prevent alloepitopic stimulation of responsive T cells.

Active immunotherapy is not particularly preferred, as it cannot be guaranteed that all of the antibodies raised in response will necessarily recognize virus or alloresponsive T cells receptors. Preferred active immunotherapy uses such substances as those defined under 'Peptides' hereinbelow. However, active vaccines may be used to sustain immune blockade or suppression of alloresponsive T cells, for example. Continued maintenance of suppression of alloreactive T cell clones is a preferred long term therapy, as this ensures that no new alloresponsive clones emerge.

Immunotherapy to eliminate susceptible T cell clones may also be used in instances where there is a high risk of developing AIDS in individuals where the patient is $HIV^+$ but exhibits no symptoms of AIDS.

Passive Immunotherapy

Passive immunotherapy is generally preferred, as the content of the vaccine is known, and effective antibodies will be immediately available to eliminate alloreactive T cells, for example, without having to wait for a second response to the components of an active immunotherapy.

The antibodies of the passive immunotherapy may also be linked to suitable toxins or complement activators to further enhance anti-T cell action, or to destroy cells bearing the alloepitope, for example.

Suitable toxins are well known in the art, and may comprise toxic radioisotopes, heavy metals and enzymes, as well as such natural toxins as ricin, which are capable of acting at the level of only one or two molecules per cell.

Other Considerations

Other considerations are generally as described for 'Vaccines' above, including methods for raising suitable antibodies, variation of antibody type in individual vaccines, dosage form and the like.

It will be appreciated that antibodies for use in accordance with the present invention, whether for diagnostic or therapeutic applications, may be monoclonal or polyclonal as appropriate. Antibody equivalents of these may comprise: the Fab' fragments of the antibodies, such as Fab, Fab', F(ab')$_2$ and Fv; idiotopes; or the results of CDR grafting, for example. Other suitable modifications and/or agents will be apparent to those skilled in the art.

DIAGNOSTIC APPLICATIONS

The present invention also provides diagnostic techniques for the detection of alloresponsive T cell receptor, HIV or substances recognizing either, such as antibodies.

Any substance of the invention may be used in a suitable diagnostic technique, although discussion will be generally limited to antibodies. The techniques of the invention are not so limited.

The various moieties which it will generally be most desired to detect include HIV, alloresponsive T cell receptor and anti-HIV antibodies.

Detecting HIV

The antibodies appropriate for detecting HIV will be those which recognize an alloepitope of HIV gp160 or one or more products thereof. The usefulness of such a technique will tend to be limited, owing to the fact that other techniques are commercially available, and which can more generally detect HIV. However, an advantage of the present technique for diagnosing HIV may lie in using the technique in combination with a more general diagnostic technique. If the latter technique diagnoses HIV, but that of the invention does not, then the infection is unlikely to lead to AIDS, as T cells alloepitopically-reactive towards the infective strain do not appear or occur in the patient.

Detecting alloresponsive T cell receptor

Of more general applicability is a technique for the detection of alloresponsive T cell receptor. Detection of gp120 alloresponsive T cell receptor is indicative of whether an individual is susceptible to HIV-induced AIDS, the presence of alloresponsive T cell receptor being diagnostic of susceptibility.

Individuals may be screened at any time for the presence of alloresponsive T cell receptor. If alloresponsive T cell receptor is found, especially in high frequency, in individuals, in the absence of HIV infection, then suitable action, if desired, can be taken to avoid infection or prevent AIDS, such as the administration of a preparation to eliminate susceptible T cells as described above.

Role of Peptides in Screening for alloreactive T cell Receptor

Peptides resembling the α-helix of gp120 may be used to detect alloresponsive T cell receptor directly. Such peptides may bind with variable affinity to the T cell receptor of alloresponsive T cells when presented on a suitable vehicle (such as a red cell). Such peptides will promote resetting of T cells expressing T cell receptor specific for the peptide, but not with unreactive T cell receptors. Quantitating the peptide-binding T cells give a direct indication of their prevalence in the individual, and indicates which individuals will be susceptible to AIDS when infected with HIV. Using the peptides diagnostically may prove preferable to bioassays dependent upon measuring T cells proliferative responses in naive subject presented with gp 120 upon a carrier (usually a cell) or a virus particle.

Diagnosis of susceptibility to AIDS development may also be performed after infection, even when AIDS is evident, although, in this case, use would generally be limited to monitoring therapeutic effects. In the former instance, lack of alloreactive T cells is indicative that the HIV + patient will not develop AIDS, as he does not possess a T cell population alloreactive to gp120. Accordingly, no treatment will be required for such individuals, although it would generally be advisable to monitor such people against the development of alloreactive clones at a later stage.

Techniques

Thus, the invention provides a diagnostic technique for the detection of a substance selected from the group consisting of:

a) an alloepitope of HIV gp160 or one or more products thereof;

b) CD4+T cell receptors recognizing an alloepitope of HIV gp160 or one or more products thereof;

c) substances which recognize an alloepitope of HIV gp160 or one or more products thereof; and d) substances which recognize CD4+T cell receptors recognizing an alloepitope of HIV gp160 or one or more products thereof;

said alloepitope being associated with gp160, or one or more products thereof, when presented on a cell membrane, and which, when so presented in a CD4+T cell proliferation assay, stimulates proliferation of at least one CD4+T cell clone, said technique comprising bringing an assay sample into contact with an assay substrate which either:

a) recognizes an alloepitope of HIV gp160 or one or more products thereof, or b) recognizes CD4+T cells receptors recognizing an alloepitope of HIV gp160 or one or more products thereof, said substrate not recognizing a CD4+T cell receptor which preferably does not recognize said alloepitope, said assay substrate being selected according to the substance which it is desired to assay, and subsequently assaying binding of said substrate.

Suitable techniques for performing diagnoses are well described in the art.

These may vary from simple qualitative techniques, merely intended to establish the presence or otherwise of the target alloepitope, to generally more complex quantitative techniques.

Tests for the presence of absence of alloresponsive T cell receptor, for example, may simply comprise use of a prepared T cell sample, contacting the sample with a labelled preparation of the appropriate antibody, and then washing off excess antibody. Remaining antibody can then be detected as appropriate, such as by FACS analysis, fluorescence microscopy or other techniques, as described below.

Qualitative and well known antibody-based techniques include, for example, ELISA (enzyme linked immunosorbent assay); one or two-step RIA (radioimmunoassay), and sandwich RIA. Any conventional procedures may be employed for such immunoassays.

Procedures may suitable be conducted such that: a suitable gp120 or T cell receptor standard, for example, is labelled with a radioisotope, such as $^{125}I$ or $^{35}S$, or an assayable enzyme, such as horseradish peroxidase or alkaline phosphatase, and, together with the unlabelled sample, is brought into contact with the corresponding antibody, whereon a second antibody is used to bind the first and radioactivity or the immobilized enzyme assayed (competitive assay); alternatively, gp120 or T cell receptor in the sample is allowed to react with the corresponding immobilized antibody, radioisotope- or enzyme-labelled anti-gp120 or anti-T cell receptor antibody is allowed to react with the system and radioactivity or the enzyme assayed (ELISA —sandwich assay). Other conventional methods may also be employed as suitable.

The above techniques may be conducted essentially as 'one-step' or 'two-step' assay. The 'one-step' assay involves contacting antigen with immobilized antibody and, without washing, contacting the mixture with labelled antibody. The 'two-step' assay involves washing before contacting the mixture with labeled antibody. Other conventional methods may also be employed as suitable.

Enzymatic and radio-labelling of gp120 or T cell receptor and/or the antibodies may be effected by conventional means. Radio-labelling of tyrosine groups may suitably be effected by exposure of the protein to an enzyme such as glucose oxidase, or another mild oxidative agent, such as Chloramine T, in the presence of radioactive iodine, suitably in the form of $^{125}$I-labelled sodium iodine.

Other labelling means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple exposure to polystyrene can be suitable to provide a support.

Enzymes employable for labelling are not particularly limited, but may be selected from the members of the oxidase group, for example. These catalyze the removal of an electron from $O_2$ generating oxidative activity, as measured by color change. Reductive enzymes can also be employed.

Other techniques include Western blotting (Towbin et al., Proc. Nat. Acad. Sci. (1979), 76, 4350), wherein a suitable treated sample of gp120 or T cell receptor, for example, is run on an SDS PAGE gel before being transferred to a solid support, such as a nitrocellulose filter. Anti-gp120 or anti-T cell receptor antibodies (unlabelled) are then brought into contact with the support and assayed by a secondary immunological reagent, such as labelled protein A or anti-immunoglobulin (suitable labels including $^{125}$I, horseradish peroxidase and alkaline phosphatase).

Besides enzymes, other suitable labels include radioisotopes, such as iodine ($^{125}$I, $^{121}$I), carbon ($^{14}$C), sulphur ($^{35}$S), tritium ($^3$H), indium ($^{112}$In) and technetium ($^{99m}$Tc), fluorescent labels, such as fluorescein and rhodamine, biotin, and phycoerythrin.

Samples for diagnostic purposes will generally be obtained from the bloodstream or lymphatic system, although other sources may be used, if desired.

Should in vivo imaging be desired, then markers suitable for this purpose may be any that do not substantially interfere with the antibody binding, and which allow external detection. Suitable markers may include those that may be detected by X-radiography, NMR or ESR. For X-radiographic techniques, suitable markers include any radioisotope that emits detectable radiation but that is not overtly harmful to the patient, such as barium or casium, for example. Suitable markers for NMR and ESR generally include those with a detectable characteristic spin, such as deuterium, which may be incorporated into the antibody by suitable labelling of nutrients for the relevant hybridoma, for example.

In the case of in vivo imaging methods, an antibody or antibody fragment which has been labelled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the subject to be examined. The quantity of radioactivity injected will normally range from about 5 to 20 millicuries of technetium-99m, for example.

PHARMACEUTICAL APPLICATIONS (A) POLYIONIC ANTI-HIV COMPOUNDS

The present invention further provides compounds interactive with the characteristic charged region of the α-helix of gp120 corresponding to the major α-helix of MHCCII. These compounds are capable of blocking the alloreactive induction of T cells by membrane bound gp160.

Uses

Such compounds are of use as anti-AIDS drugs. The molecular configuration of the compounds is such that the compounds interact with or bind the alloepitopic region of gp120. Accordingly, administration of these compounds to a person with an HIV infection serves to prevent the development of AIDS by blocking recognition of the gp120/gp41 alloepitope by the T cell receptor.

Guided Design

A particular advantage of the invention is conferred by the ability to generate drugs specific for HIV, in the knowledge that such drugs need no longer be found by empirical research, and in the knowledge that MHC will be affected little, if at all.

Caveat

As described above for vaccines, it is not generally desirable to so engineer the compounds as to be able to bind MHCII, as this will dilute the efficacy of the compounds, and may actually have a deleterious effect on the immune system, although the first of these factors is likely to be of more significance.

Relevance of Gp120 Structure

As has also been mentioned above, the major α-helix of gp120 is in close spatial proximity to the CD4 binding region of that molecule, so that large or long compounds interacting with the α-helix also serve to sterically hinder and block CD4 binding. This is a particularly preferred feature of the invention. It is likely that it is just such an effect that accounts for the anti-HIV effect of dextran sulphate.

The major α-helix of gp120 is in the general area of AA 496–508; and corresponds to the region of MHCI in the area of AA 152–165; and to the region of MHCII in the area of AA 68–81. While the α-helices are generally referred to as corresponding to specific residues, it will be appreciated that such secondary structures cannot be specifically defined as starting at a precise residue and finishing at a precise residue, as there will be conformational constraints and other forces which must be taken into consideration. However, the α-helices of the molecules are generally located in the regions defined.

Seven of the thirteen amino acids in the gp120 α-helix are basic (positively charged) and the five arginine side chains of these project from the bottom face of the helix (AA 152–165 of MHCI and AA 67–81 of MHCII include one and two arginine residues, respectively).

The major α-helices of the MHC molecules have a group of basic residues projecting from one face, and gp120 has a corresponding group, but it also has a further group on a face rotationally removed from the first. Both groups are implicated in T cell receptor binding, and this second group is highly conserved. Accordingly, it is preferred that the compounds of the invention are so engineered that at least one residue of this second group is recognized and bound.

Figure 9:
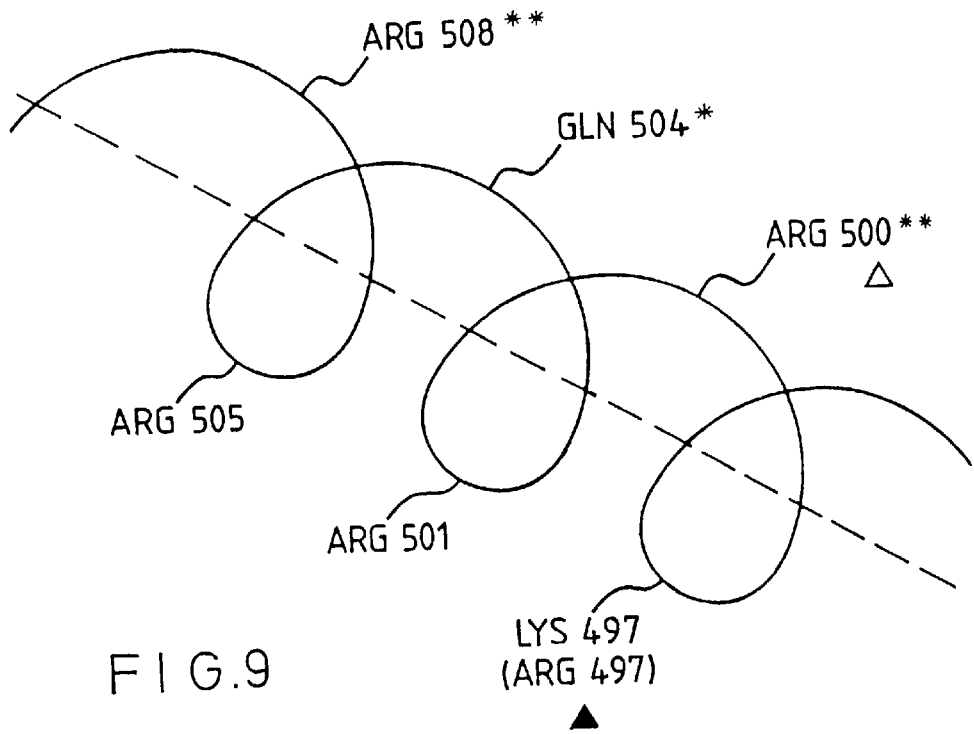
FIG. 9 is a simplified diagram of the α-helix of gp120 glycoprotein.
Figure 10:
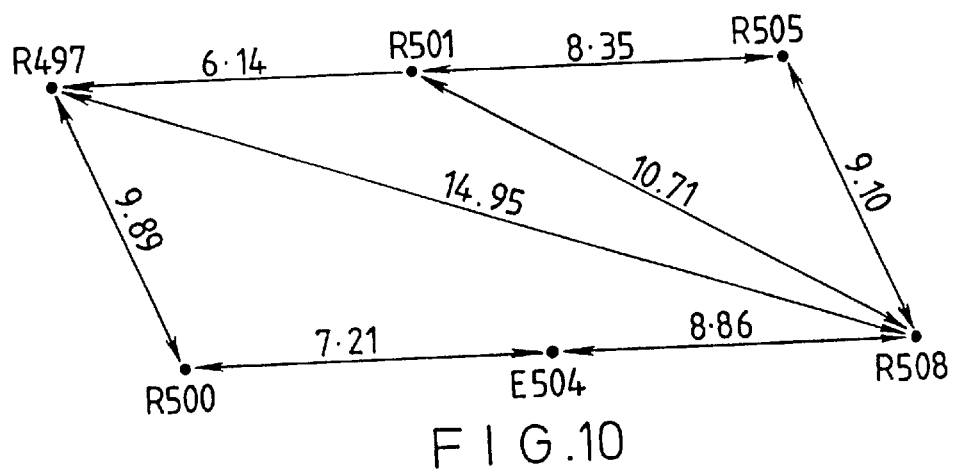
FIG. 10 illustrates the distances between the residues shown in FIG. 9.

In the accompanying FIG. 9, the α-helix of gp120 is shown in simple diagrammatic form. The residues labelled with the open triangle correspond to those of the MHC molecules, the asterisks indicating degree of homology. One asterisk indicates a similarity, rather than direct homology. Those residues labelled with the solid triangle are characteristic of gp120, and these residues are depicted as appearing on a different face of the α-helix. A residue in brackets indicates an alternative residue that occurs in some isolates. It will be appreciated that the representation of FIG. 9 is purely diagrammatic, and is only indicative of the general topology of the region of gp120.

The apparently important residues of gp120 in the 496–508 sequence are in the positions 497, 501 and 505. They are lysine (or arginine), arginine and arginine, respectively, in all isolates studied. In addition, the face of the helix corresponding to the charged face of the MHC major α-helix has arginine, glycine and arginine in positions 500, 504 and 508, while, in MHCI, the corresponding residues are Arg, Glu, Val and, in MHCII, are Arg, Asp, Arg.

Comparison between Gp120, MHCI and MHCII

The formula below aligns the sequence of AA496 508 of gp120 with those of MHCI (HLA A2) and MHCII (DR31), having specific regard to the non-polymorphic residues recognized by the T cell receptor (shown by asterisks).

Thus, the charged residues of gp120 in the major α-helix region permit interaction with other charged groups, such as sulphates, so that compounds interacting with these groups can be used to block T cell recognition of gp120/gp41 alloepitopic structures, and thus prevent AIDS development.

Definition of Drugs

In accordance with the present invention, there is provided an anti-HIV effective compound, the compound being characterized in having charged groups, the charged groups being complementary to the characteristic charged groups of the major α-helix of gp120 and adopting such a conformation that interaction with the characteristic charged groups of HIV gp120 in the region 496–508 occurs.

By 'characteristic' is meant those charged groups defined above with respect to MHC, and may include any or all residues characteristic of MHC provided that at least one characteristic residue of gp120 is bound by the compound.

By 'complementary' is meant a group having such a charge as to attract the relevant charged group of gp120. It is not necessary, and not even necessarily desirable, to target all of the characteristic charged groups of gp120, and neither is it necessary that only one charged group of the compound should correspond to the targeted gp120 group, although this is preferred.

In general, it is preferred to provide those compounds which either recognize only those residues characteristic of gp120, or which must recognize at least one characteristic residue of gp120 to bind. If two or more residues of MHC can be recognized by the compound, then there is a possibility that MHC rather than HIV will be targeted, possibly deleteriously affecting the immune system, and diluting the effect of the compound. Such a possibility may be avoided by the use of steric hindrance or suitable blocking groups, but it is preferred to exclude recognition of MHC altogether.

It is from this aspect that a particularly preferred compound would be so constrained as to recognize glutamine 504 of gp120. The corresponding residues in MHCI and MHCII are glutamate and aspartate, so that an acidic residue in the compound of the invention would negatively interact with MHC but positively interact with gp120.

Again, as with vaccines, it is important to appreciate that, while just one compound can be used to treat a patient, it is

```
                * *     * *     *     * *
Class I   V A E Q L R A Y L E G T C V (SEQ ID NO. 2) (152-165)

Class II  L L E Q R R A A V D T Y C R (SEQ ID NO. 3) (68-81)
              □     ▽ □   ▽ □     ▽

GP120     T R A K R R V V E R E K R (SEQ ID NO. 4) (496-508)
```

The above sequence for gp120 is a further preferred sequence for use in the present invention.

Each amino acid of the underlined doublets projects from one of two adjacent faces of the relevant α-helix respectively (for a discussion for class I and II, see Brown, et al. (Nature 1988, 332;845)). Those important residues which project from the two faces of the helices are indicated by □ and ▽, distinguishing between the two faces.

The sequence of gp120 AA496–508 should adopt a 'perfect' 5-fold helix solution, the amine groups of R497, 501 and 505 being essentially planar and separated by a distance of the order of 0.5 nm. These distances are similar to the distances separating particular sulphate substituents of oligosaccharides, and provide a convenient target for drug design.

preferred to use a combination of compounds adapted to recognize different characteristic residues of gp120 in order to minimize the risk of resistant strains developing.

To avoid resistant strains developing, it may be advantageous to target residues R500 and R508 of gp120. The asparagine residues in these positions are important for T cell receptor recognition of MHC, and the evidence suggests that these residues are essential in T cell receptor recognition. Accordingly, if gp120 defensively mutates to avoid a compound interacting with either or both residues, then it will no longer be able to induce AIDS, as the gp120 molecule would no longer mimic MHC.

In the proposed 5-fold helix structure for gp120, the side chain of R508 is aligned with R497, 501 and 505 whereas R500 has a similar orientation to the two other basic residues K499 and 507, so that preferred compounds target these sets of groups.

The types of compounds usable in accordance with the present invention are any which can provide a suitably charged moiety able to adopt the correct configuration to interact with gp120.

The compounds will generally comprise a substantially neutral backbone supporting at least two charged groups adapted to interact with charged groups on gp120. Certain compounds of the invention may be so designed as to have highly flexible backbones which are capable of adopting many configurations in solution, and which can allow specific conformations for the charged side chains to bind gp120. Such backbones will generally be polymeric in nature, with single bonds between units, and little steric hindrance.

Other backbones may be so designed as to be effectively rigid, so that the precise orientation of the charged groups thereon can be calculated and placed according to requirements.

The charged groups are not limited, but may be any that will serve to positively interact with, or attract, the charged groups of gp120. Any generally negatively charged group may suffice for most groups, although it will be appreciated that a positively charged group would be required to interact with glutamine 504.

Preferred side-chains are the strongly charged sulphate and phosphate groups, for example, while the molecule on which they are substituted is preferred to be a non-toxic polymer, such as polyvinyl or polyvinyl alcohol polymer, or an oligo- or polysaccharide. The sub-units from which such polymers may be constructed vary very widely, so that virtually any configuration may be constructed to interact with virtually any relevant charge configuration.

Due to the large diversity of monosaccharides which can be called upon to provide virtually any fit, and to the ability to alter the sulphate substitution pattern by chemical synthesis, this group of compounds is particularly preferred for obtaining the correct molecular dimensions.

By varying the sulphation pattern and monosaccharide composition it is also possible to design a ligand reacting with slightly less constrained helical conformers to increase the distance between R497, 501, 505.

Further, as the α-helix of gp120 is spatially close to the CD4 binding loop of gp120, longer oligomers or polymers can extend to block the CD4 binding site, and provide a preferred feature of this aspect of the invention.

Thus, the present invention envisages both short and long chain polymers with charged side chains. With longer compounds, the area of gp120 recognition may be unique within the molecule, or may be repeated, optionally with non-interactive regions interspersed with interactive regions, either regularly or irregularly. In addition, in even one compound, there may be more than one variety of gp120-interactive region.

Other Compounds

It will also be appreciated that similar compounds may be prepared that will bind and block alloresponsive T cell receptors. Such compounds will not necessarily be able to bind those which bind gp120, but will have, at least partially, a similar charge configuration to that of characteristic residues of gp120. Compounds of this nature are described in more detail in 'Peptides,' below.

It will be appreciated that at least some of the compounds described in this section may be used in vaccines, immunotherapy or diagnostic techniques as defined above. Those that are suitable are readily identifiable by those skilled in the art, and such applications are included in the scope of the invention.

(B) PEPTIDES

The present invention further provides peptides and related compounds intercoactive with the T cell receptor or alloresponsive T cells. These compounds can be used to inhibit or block the alloreactive response of T cells to membrane bound gp160 (gp120/gp41). Such compounds are generally peptides, although the present invention also extends to compounds comprising peptides, and to compounds which are not peptides, but which present at least some of the characteristic features of peptides as defined hereunder. In particular, provided that the said substance has substantially the same or similar effect to the peptide when used in place of the peptide, then it is defined herein as being the equivalent of the appropriate peptide.

As used herein, 'peptide' is any compound containing at least one peptide linkage, and includes oligopeptides and polypeptides.

Definition

Accordingly, there is provided a molecule comprising a peptide, the peptide exhibiting at least one stretch of α-helical secondary structure from which project at least two charged residues in positions on the helix, such that the residues and their positions correspond to residues and their positions in one or more peptide sequences selected from the following: gp120 in the area of AA 496–508; MHCI in the area of AA 152–165; and MHCII in the area of AA 68–81, provided that at least one of the charged residues corresponds to a residue of gp120 as defined and that such residue does not correspond to a residue of either MHCI or MHCII as defined.

The term 'correspond' is used to indicate a residue and/or its position which is the same as or equivalent to the residue in the specified sequence. An equivalent residue or position need not be exactly the same as its counterpart in the specified sequence, provided that it is sufficiently similar for the purposes to which it is intended to put the peptide that the same end result will be achieved as if the residue or position had been the same. An example may be where a different acidic residue is used to simulate aspartate.

The α-helical structure is preferably one that will tend strongly toward such a structure in the absence of other considerations. Structures which only weakly form α-helices may also be used, but it may be advantageous to use them in an environment where the formation of α-helical structure is facilitated or encouraged.

The primary sequence of the α-helix can be any that is suitable, as described above, but a preferred sequence is that of an MHC major α-helix or the corresponding gp120 α-helix, as defined. In any event, it is preferred only to use charged residues corresponding to those of the specified sequences and no others. The residues and their positions are preferably the same as any to which they correspond in the sequences defined above.

Important peptide sequences

The important sequences and residues of gp120 are defined above in 'Polyionic Anti-HIV Compounds.' Taking such important residues into consideration, a number of sequences becomes apparent which may be of most use.

Essentially, it is preferred to use the α-helix backbone of MHCI or MHCII. The charged residues then correspond to those of MHCI or MHCII. A mixture of the charged residues may be employed from the two classes, but this is not generally preferred, as spurious antibodies to non-existent entities may arise. The peptide then further incorporates one charged residue characteristic of gp120. It will be appreciated that this yields 6 preferred sequences—3 each for MHCI and MHCII incorporating one each of residues 497, 501 and 505 of gp120.

The α-helix backbone may be substituted, for example, with alanines instead of one or more of the MHC charged residues, giving rise to a further 8 basic helix backbone possibilities. These, as well as the unsubstituted backbones, may then be substituted with one or more residues characteristic of gp120. Where there are 0 or 1 residues characteristic of MHC, it may be preferable to incorporate 2 or 3 gp120 residues.

Arg 500 of gp120 appears to be particularly important for the alleopitopic effect of HIV, and so peptides possessing this residue are particularly preferred. This residue corresponds to Arg 73 of MHCII and Arg 157 of MHCI. Also important appears to be Arg 508 of gp120, corresponding to Arg 81 of MHCII and Val 165 of MHCI. Peptides incorporating both of these residues are particularly preferred. That peptide which has a residue corresponding to glutamine 504 of gp120 instead of the aspartate or glutamate residues of the MHC molecules may be particularly useful.

The peptides of the invention may be used, as appropriate, in any of the other of the aspects of the invention, such as in the preparation of vaccines, raising antibodies, blocking T cell receptors and other uses as will be apparent to those skilled in the art.

DRUG ASSAYS

The present invention also provides a method for the testing of potential anti-HIV-induced AIDS therapies.

Specifically, with the knowledge that gp120, or gp160, is acting as an alleopitope, we have discovered that it is possible to generate CD4+T cell lines which proliferate only when presented with cells expressing gp160. Such cells are defined herein as being gp120 restricted.

The Assays

Accordingly, the invention provides a system comprising of gp160-expressing cell line and a gp160 restricted cell line for use in assaying the anti-HIV effect of any given substance. The invention also provides the use of such a system in an anti-HIV assay, as well as the preparation of such a system, which optionally includes the preparation of suitable cell lines.

Methods for the preparation of suitable cell lines are described herein, including a specific Example (Example 6).

It will be appreciated that references to gp120 and gp160 are in the same nature as elsewhere herein, and are essentially interchangeable.

Uses

The assay systems of the invention are particularly useful in establishing the usefulness of new drugs in the inhibition of HIV-induced AIDS development, and provide a ready and simple technique. If the potential drug is added to the system, but the gp160 alloreactive T cells still proliferate, then it is very likely that the drug has no useful activity in prevention of AIDS, at least in the form tested.

On the other hand, if proliferation is blocked or reduced, then this is a strong indication of primary activity in preventing HIV-induced AIDS by inhibition or blocking of T cell alloreactivity towards gp120/gp41.

The following Examples serve to illustrate the invention only, and should not be construed as limiting it in any way.

EXAMPLE 1

Constructing Reverse Transcriptase Deficient HIV (RTM)

RTM proviral DNA was constructed by transformation of competent *E. coli* with shuttle expression vectors containing the ampicillin gene, for selection in *E. coli,* and the gpt gene, for selection in mammalian cells, and either the full length infectious clone of HIV strain HX2B (pHXB2gpt) or a clone containing only the gag, pol, and sor genes between the two viral LTRs (pHXB25'gpt).

Using the restriction enzyme Kpnl, a 528 nucleotide fragment was removed from the reverse transcriptase sequence of the pol gene in pHXB25'gpt (full length proviral DNA contains additional Kpnl sites). After ligation, several attempts at transforming *E. coli* were required before a colony was contained that did not have deletions or rearrangements in the HIV DNA sequences. The *E. coli* used for transformation were strains such as DH-1 and JM109 that are recombinase minus and, therefore, not theoretically capable of deleting or rearranging cloned DNA.

Upon retransforming *E. coli* using pHXB25'gpt (with the 328 bp Kpnl fragment deleted), of 24 colonies examined, only one did not contain a deletion or a rearrangement. Thus, it appeared that the construct made had unusual secondary or tertiary structure incompatible with the *E. coli* used. According to Le et al. (1088 N.A.R. 16:5153) the region of HIV from which the 328 bp fragment had been removed is, in fact, a region predicted to have secondary structure.

The above construct and pHXB2gpt were then digested with the restriction enzyme Ball and its isoschizomer Mscl. This was to release a 1.9 kbp fragment from pHXB2gpt that could be replaced by a 1.6 (minus 328 bp)kbp fragment from pHXB25'gpt-Kpnl. Examination of the ligated plasmid and insert on electrophoresis gels showed ligations to have worked well. However, despite numerous redigestions and ligations, no colonies were ever obtained upon transformation into several different strains of *E. coli* (DM1, JM109, NM522, DM5 and SSC1) although successful transformations with digested and religated control plasmid were performed.

Since Ball and Mscl are blunt end cutters, and ligation of blunt ends is less efficient than of sticky ends, a new restriction digestion regime that would release the correct fragment from pHXB2gpt and allow replacement with the 328 bp deleted fragment from pHXB25'gpt-Kpnl was sought. However, transformation of the same range of *E. coli* produced no colonies at all, even though gels showed ligation to be efficient. Since similar intransigence had been encountered with the initial cloning of pHXB25'gpt-Kpnl it was concluded that the structure created by the deletion in the reverse transcriptase gene, coupled with the secondary structure reported in the env gene, were too much for the *E. coli* to cope with. The construct was, apparently, an unclonable piece of DNA.

A strain of *E. coli,* manipulated to clone unclonable DNA by removal of genes that recognize and edit secondary and tertiary structure in DNA, then became available, and repetition of transformation gave colonies containing pRTM DNA, without any problem (a plasmid containing the proviral DNA encoding the deletion mutant of HIV, identified as pRTML, and carried in *E. coli* strain SURE [TM Stratagene, 11099 North Torrey Pines Rd, La Jolla, Calif. USA] was deposited on 12 Oct. 1990 at the National Collection of Type Cultures, 61 Colindale Avenue, London NW9 5HT, UK, Deposit No. NCTC 12424, under the terms of the Budapest Treaty).

The delection introduced into pRTM also causes a frame shift so the virions produced by transfection contain a truncated reverse transcriptase and no integrase. The virions produced by the pRTM DNA may be characterized by: RIPA (radioimmunoprecipitation assay); Western Blotting; P.R.R. across the 328 bp deletion; E.M. and syncytial assay.

EXAMPLE 2

Generation of HIV gp120 Restricted T Cell Lines

Peripheral blood leukocytes from a single donor are transfected with reverse transcriptase deficient mutant HIV (prepared in Example 1).

These HIV gp120 expressing cells are used as the syngeneic feeder cell component of T lymphocyte cultures, as follows:

(a) Cells are checked for appropriate expression of virions and of gp120;

(b) Cells are irradiated;

(c) Cells are then added to cultures of syngeneic peripheral blood T lymphocytes ($3 \times 10^4$ feeders to $1 \times 10^6$ PBL in RPMI or ISCOVES medium supplemented with 10% autologous serum or plasma) in 24 well cluster plates;

(d) After 4 days culture, proliferating cells are split, diluted 1:4, and fresh transfected irradiated syngeneic feeder cells added;

(e) After a further 7 days culture, recombinant IL-2 (30 $\mu$/ml) is added and culture continued for a further 7 days;

(f) This protocol is continued for a further 3–4 cycles until the resulting T cell lines are relatively homogeneous; and (g) T cell clones are derived from these bulk T cell lines, by diluting to 0.5 cells/well and seeding into 96 well microtitre plates containing $3 \times 10^4$ irradiated transfected feeder cells/well.

(2) Generation of Antigen Specific gp120 Restricted T Cell Lines

The T cell lines generated in (1) are not necessarily gp120 specific, nor gp120 restricted. Both of these parameters need to be fulfilled before appropriately allospecific gp120 restricted T cell clones can be derived. Thus, the second step involves a different stimulator; murine P815 cell line or CHO cell line transfected with HIV gp160. Using this artificial construct, gp120 alloresponsive (alloreactive) clones can be defined, and antigen-specific gp120 restricted clones generated.

(2a.1) Cloned T cells, or bulk T cell lines from (1) are co-cultured with irradiated P815 or CHO cells, (expressing both gp120 and gp41 from endogenously cleaved gp160);

(2a.2) Proliferating T cells are obtained by the method described in (1) and cloned. These T cells constitute gp120 alloepitope specific T cell lines.

In the alternative:

(2b.1) Cloned T cells, or bulk T cell lines from (1) are co-cultured with $3 \times 10^4$ irradiated gp160 transfected P815 or CHO cells, previously pulsed with either Tetanus Toxoid, purified protein derivative (PPD), or candida;

(2b.2) After exposure to antigen for 4–5 days, cultures are stimulated by recombinant IL-2 (30 $\mu$/ml), for a further 7 days;

(2b.3) Cultures are split 1:4 and fresh irradiated antigen pulsed gp160 transfected P815 or CHO cells added;

(2b.4) This protocol is continued for a further 3 or 4 cycles. Clones may subsequently be generated by dilution as in 1.g.

The resulting lines are antigen specific gp120 restricted.

(3) Assays for Homogeneity of Response of Cell Lines Generated in Protocols 1 (a-g), 2a (1-2), 2b (1-4)

Each cell line can be tested for its proliferative response in the following assays.

(3a) Response to Syngeneic APC (1 AND 2a) or Antigen Pulsed Syngeneic APC (2b)

(i) To $20 \times 10^3$ IL-2 stimulated T cells derived from protocols 1 and 2a are added $50 \times 10^3$ irradiated syngeneic PBL. These are co-cultured 24 hours without IL-2;

(ii) $H^3$ Thymidine is added (incorporated into DNA of proliferating cells), and culture is continued for 24 hours ($1.85 \times 10^4$ Bq $H^3$ T);

(iii) Cells are harvested and counted.

For antigen pulsed syngeneic APC, the lack of response measured indicates the degree of T cell restriction to gp120, in association with TT, PPD or candida. The T cell lines (prepared by protocol 2b) will not proliferate when exposed to syngeneic APC not pulsed with antigen.

When syngeneic APC are pulsed with antigen, a proportion (but not all) of the clones generated by protocol 2b will respond to antigen. These "bifunctional" clones are antigen specific but neither MHC restricted nor gp120 restricted.

(3b) Response to HIV RT—Transfected Syngeneic Antigen Presenting Cells

In this experimental protocol, there is a distinction made between clones derived by protocol (1) which are gp120 alloreactive, and clones reacting to some other component of HIV.

(a) Syngeneic APC are transfected with HIV RT mutant virus;

(b) $20 \times 10^3$ T cells from experimental protocols 1, 2a, and 2b, are cultured for 24 hours in the absence of IL-2;

(c) To $20 \times 10^3$ T cells are added $50 \times 10^3$ transfected irradiated (30Gy) APC in 0.2 ml in 96 well microtitre plates; and (d) The cells are pulsed with $H^3$ thymidine ($1.85 \times 10^4$ Bq: Sp. A. $1.85 \times 10^{10}$ Bq/mole) and harvested 24 hours later.

Using this assay, T cells prepared according to protocol 1 and 2a will proliferate, while T cells prepared according to Protocol 2b will not proliferate.

(3c) Proliferation of Cells Prepared by Protocol 2b

An assay is performed as described in protocol 3b, but the syngeneic, HIV RT transfected APC are antigen pulsed with either TT, or with PPD.

T cells prepared according to protocol 2b will proliferate in this assay, indicating specificity for HIV gp120, and restriction to gp120.

(4) Characterization of TCR on T Cell Clones of the Following Types (1) gp120 alloreactive clones (2a)

(2) gp120 restricted clones (2b) and (3) "Bifunctional" antigen specific unrestricted clones.

The TCR characteristic of these three groups of T cell clones is isolated, amplified and sequenced. Preliminary data can be obtained by study with the limited number of V$\beta$ specific monoclonals available, and by hybridization with V region probes of known sequence.

The techniques for accomplishing this are standard molecular biological procedures.

(5) Preparation of Potential Vaccines

The starting point for this procedure is the T cell clone defined as being either "atloreactive" or as being "antigen specific and gp120 restricted." It is probable that both clonal types share a common TCR structure and "idiotype."

Mice immunized with bulk T cells derived from the characterized clones are used to provide spleen cells for monoclonal antibody hybridoma production by conventional techniques. Such monoclonal antibodies constitute an $Ab_1$ reagent.

The appropriate specificity of the $Ab_1$ reagent desired is:

(a) that it reacts with all T cell clones having a common receptor for gp120 as either an alloepitope, or as a restriction element;

(b) that in assays 3a, 3b and/or 3c it prevents proliferative responses by these T cell clones; and (c) that T cells reactive with this antibody constitute part of the T cell pool of HIV seropositive subjects.

Assay of Effective Vaccines

To assay the activity of any agent considered suitable, the agent must be able to prevent proliferation of gp120 restricted T cells. A suitable assay comprises use of cells generated according to protocols 2*a* and 2*b* above, and assaying the ability of the vaccine candidate to prevent proliferation when these cells are presented with gp120 transfected CHO or P815 cells. The agent must be able to prevent proliferation of all antigen specific gp120 restricted T cells, but not MHCII restricted T cells.

Colonies of relevant clones can be maintained by occasional exposure to gp120 transfected CHO or P815 cells pulsed where necessary with the relevant antigen (where the clone is antigen specific) . Use of clones specific for 3 antigens (PPD, TT and candida) ensures that any restriction to gp120 is specific, and not due to antigen cross reactivity.

The advantage of using rodent cells to maintain the clones lies in the fact that naive human T cells are not effectively stimulated by rodent MHC presented on the transfected cell membrane. The use of two or three combinations of transfected cell, i.e. syngeneic HIV RT-transfected APC, CHO cells transfected with gp160, and P815 transfected with gp160 also alleviates the problem of confusing gp160 "alloresponsiveness" with reactivity towards rodent MHC.

EXAMPLE 3

Reactivity with Monoclonal Antibodies

Fifteen monoclonal antibodies directed against MHCI and MHCII have been studied for their effects upon gp120 binding and virus syncytial inhibition. One MHCII specific monoclonal reacts directly with gp160. In syncytial inhibition studies, MHCI specific monoclonals prevent syncytial formation. There are reports of anti-MHCI and anti-MHCII antibody activity in sera cross-reacting with gp120 or gp160. Although this data is currently weak, the fact that conformation of the protein is recognized by antibody, and not its sequence, suggests that gp120/160 has in part the conformation of MHCI or MHCII molecules.

EXAMPLE 4

TCR V Region Selection by GP160-Expressing CHO Cells

CHO cells (CHO K-1) were transfected with HIV-gp160 gene coupled to the glutamine synthetase gene. High levels of expression of the CS gene are ensured by culture in glutamine deficient medium containing methionine (G-MEM-MET) supplemented with methionine sulphoxamine (MSX). Concentrations of MSX of 0.8 mg/ml promote detectable membrane and cytoplasmic expression of gp160 by the immunoperoxidase ABC technique. The transfected cells were irradiated (30 gy) before use as stimulators.

Peripheral blood lymphocytes (PBL) from a single donor (which did not respond to gp120 when presented as an antigen in a syngeneic system) were stimulated by the addition of $1\times10^3$ gp160 expressing cells to wells containing $1\times10^4$ ficoll-separated PBL. Culture was continued for 4 days. Proliferating lymphocytes were harvested, separated from dead cells by ficoll/triosil gradient centrifugation, and recultured at $1\times10^4$ per well in the presence of 30U/ml recombinant IL-2 for a further 7 days. This cycle (4 days stimulation, followed by 7 days IL-2 expansion) was repeated twice.

V region gene expression was explored using FITC-conjugated monoclonal antibodies specific for human TCR Vβ and TCR Vα determinants. The available monoclonals detect Vβ, 5*a*, 5*b*, 5*c*,8*a*, 12*a*, 6*a* determinants, and Vα2*a* determinants. Lymphocytes from normal PBL donors and from the test subject were tested for expression of these determinants by two-color FACS analysis, using phycoerythrin-conjugated anti-CD3.

Results were expressed as percentage of CD3 positive cells also positive for Vβ or Vα determinants. Comparison of Vα and Vβ expression in the test subject before and after selection by stimulation with gp160 expressing CHO cells showed the bias in TCR expression caused by selection with gp160. In the test subject, control cultures stimulated in the same way with irradiated CHO-K1 cells without gp160 gene did not result in derivation of a proliferating T cell line. No viable lymphocytes were recoverable after the first cycle of stimulation.

Results

Expression of Vβ and Vα gene products in three normal controls (G, P, M) and in the test subject J are shown for comparison with the expression of the same V gene products in the cell line derived from PBL by stimulation with gp160-expressing CHO cells (Table 1).

As is evident, marked increase in the expression of Vα2*a* (from 1.7% to 12.8%) occurred, with smaller increases in Vβ 12*a* (from 3.0% to 7.8%), and decrease in expression of Vβ6*a* (from 10.3% to 5.6%). Comparison with normal controls illustrates quite clearly that such changes lie outside the range of variation of the four individuals tested, are therefore likely to be due to direct selection of favored Vα and β combinations by gp160. This is most markedly true for the single Vα determinant Vα2*a*.

Thus, exposure of naive T cells from one individual to irradiated CHO K1 cells expressing the gp160 HIV-1 envelope gene, for 2 cycles of stimulation, induce a bulk T cell line in which expression of the TCR determinant Vα2*a* has increased more than seven fold compared with pre-stimulated normal PBL from 4 control donors. The results, therefore, suggest that gp160 acts as an alloepitope, and probably interacts directly with the Vα chain determinant Vαa2. Alterations in Vβ expression are likewise limited to the determinants Vβ 12*a* (increased) and Vβ 6*a* (decreased). This work confirms that gp160 interacts directly with the TCR, in the manner expected of an alloepitope.

TABLE 1

COMPARISON OF Vβ AND Vα EXPRESSION IN NORMAL CONTROLS AND GP160 RESPONSIVE T CELL LINE DERIVED FROM NORMAL DONOR J

| Subjects | Vβ determinants (as % CD3 + cells) | | | | | | Vα determinant |
|---|---|---|---|---|---|---|---|
| | 5a | 5b | 5c | 8a | 12a | 6a | α2a |
| G | 9.3 | 11.5 | 4.5 | 5.6 | 1.8 | 9.5 | 1.1 |
| P | 7.6 | 6.6 | 5.1 | 10.3 | 3.7 | 6.5 | 2.1 |
| M | 6.1 | 6.6 | 3.7 | 8.4 | 3.5 | 6.8 | 1.4 |
| J | 6.9 | 7.1 | 3.2 | 8.2 | 3.0 | 10.3 | 1.7 |
| Cell Line | | | | | | | |
| J | 6.4 | 5.0 | 5.0 | 9.4 | 7.11 | 5.61 | 12.81 |

Key: ↑ significant increase, ↓ significant decrease in Vβ or Vα expression.

EXAMPLE 5

A) General Principles of 3-D Modelling MHC I/II and gp120

Many isolates of gp120 have been sequenced providing a large data base for comparison. A survey of 12 sequences identified by us and those of Modrow, et al., [1987] shows that apart from considerable homology leading up to and including cysteine residues notable regions conserved between all the isolates are as follows:

| | |
|---|---|
| 247 QCTHGI*P†VSTQLLNGSLAE (SEQ ID NO. 5) | *R or K, †V or I |
| 432 YAPPI (SEQ ID NO. 6) | |
| 444 SNITG**LTRDGG (SEQ ID NO. 7) | *L or I |
| 468 GGG*M†DNW (SEQ ID NO. 8) | *D or N, †R or K |
| 479 ELYKYKV* (SEQ ID NO. 9) | *V or I |
| 488 IEPLG*APT†AKRRVV‡REKR (SEQ ID NO. 10) | *V or I, †R or K, ‡Q or E |

These sequences include the conserved regions discussed above which have high probability to form β strands (from AA 447 to 480), areas in the so called YAPPI (SEQ ID NO. 6), SNIT (SEQ ID NO. 11), and conserved W loops, and the α helix at the C terminal end of gp120. These areas were included in our gp120 modelling aimed at elucidating the structural motifs important in AIDS pathology.

The region of HLA-A2 α3 was also included due to the significant sequence homology at the C terminus with a region of MHCII from residue 144 onwards and a highly conserved sequence of gp120 isolates around residues 255–264.

| | |
|---|---|
| HLA-A2 | 248 VVPSGQEQRY 257 (SEQ ID NO. 12) |
| DRβ1 | 144 VVSTGLIQNG 153 (SEQ ID NO. 13) |
| gp120 EL1 | 255 VVSTQLLLNG 264 (SEQ ID NO. 14) |

The homology between class I and class II continues in this region to the C terminal of HLA-A2 α3 e.g.

| | |
|---|---|
| HLA-A2 | 259 CHVQHEGLPKPL 270 (SEQ ID NO. 15) |
| DRβ1 | 175 CQVEHFSVTSPL 186 (SEQ ID NO. 16) |

The extent of homology with the α3 region of HLA-A2 suggests this may be part of a binding site for CD8 (HLA-A2) and CD4 (DRβ1).

B) Envelope Glycoprotein has an MHC-like Structure a) Molecular modelling of gp120/160 has shown features which indicate structural homology with MHCI and MHC class II. Firstly there is a conserved glycosylation site in gp120 at ASN445 in an homologous sequence to that in HLA DR. Both DR and gp120 have a homologous loop containing TRP 476. β strands occupy AA446–452 and 484–488, equivalent to the "β pleated sheet" floor of a peptide binding groove-like structure of MHC. An alpha helical structure is predicted between 496–512. Direct structural homologies exist particularly between HLA-A2 (95–101) and HLA DR 2p (15–80) and gp120 over the domain AA 442–508. Stabilization is supplied by disulphide bonds (CYS376-CYS442 and CYS385-CYS416). Further features are a) β strand between 412–415 b) possible CD4 binding domain subjacent to the MHC-like site c) conserved β bend type II at Pro 457, type I at Arg 472, ASN 445, 384, 390, 405, 409 d) β strand between 484–488 and 447–457. These are envisaged as coming together to stabilize a β pleated sheet structure. The overall configuration conforms to the α helix and β pleated sheet structure of the MHCI α chain, and the MHCII β chain with further opportunities (not modelled) of β sheet formation from the rest of the molecule (we have modelled only from AA 374–508). These data are strongly supportive of the general MHCI or MHCII orientation of the C-backbone of gp120/160.

Figure 2:
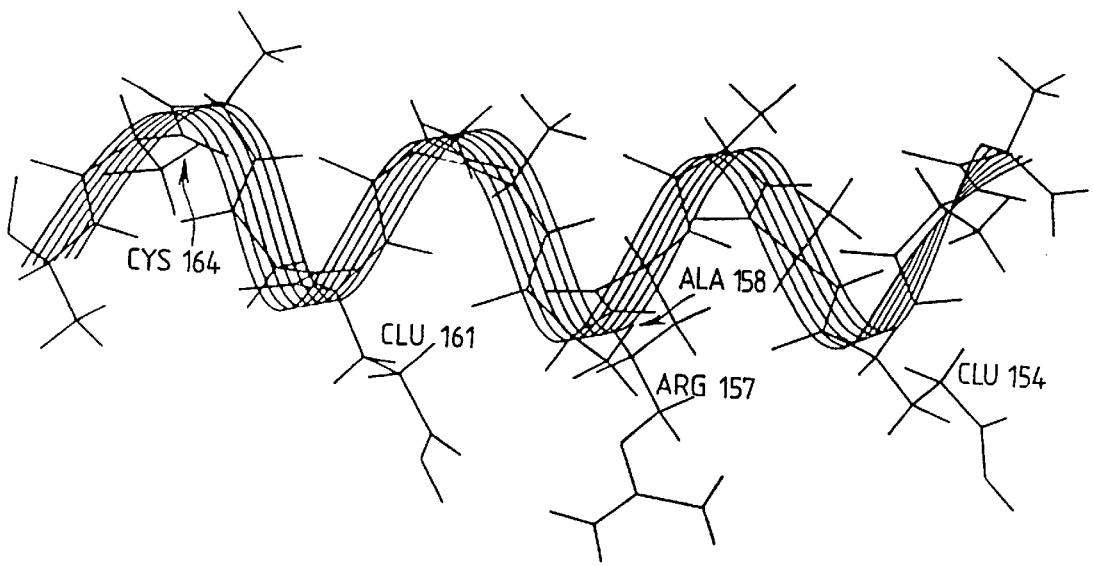
FIG. 2 is a computer-generated model of the α-helices of MHCI glycoprotein.
Figure 3:
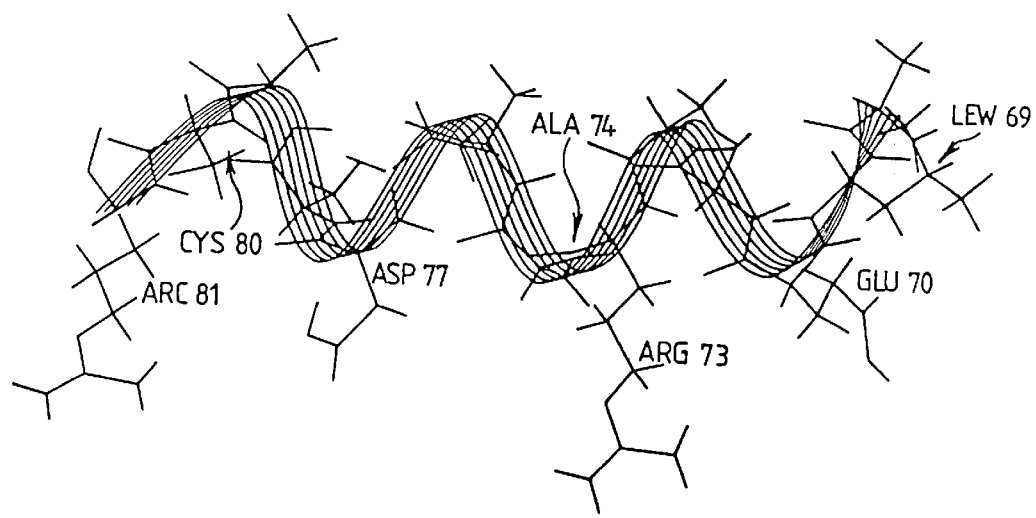
FIG. 3 is a computer-generated model of the α-helices of MHCII glycoprotein.
Figure 4:
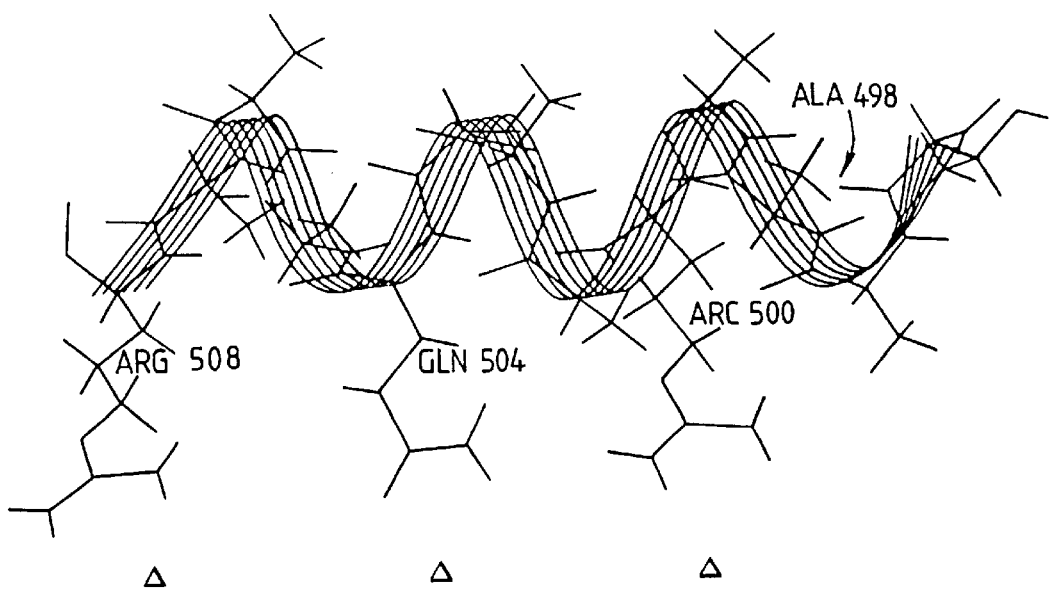
FIG. 4 is a computer-generated model of the α-helices of gp120 glycoprotein.

The computer-generated models of the α-helices of MHCI, MHCII and gp120 are shown in FIGS. 2, 3 and 4, respectively, showing the amino acid residues discussed. Other residues have been replaced by Ala for clarity. FIG. 1 shows the general structure of gp120 C-terminus and HLA-A2, high-lighting regions of similarity.

EXAMPLE 6

Detailed Molecular Modelling of gp120

In the absence of X-ray crystallographic data for gp120, the strategy we adopted was based on computer graphics molecular modelling relying on the following levels of structural comparison:

a) comparison of the amino acid sequence of the known isolates of gp120 where the conserved regions are presumed essential for CD4 binding and immune activity;

b) finding within these conserved regions sequence homologies with proteins of known 3-D structure to use as a modelling template;

c) the use of empirical protein structure prediction algorithms based on X-ray crystallographic data of non-homologous proteins to suggest areas having high probability of α helix, β strand or β turn; and d) using predicted areas of high surface probability based on hydrophilicity indices, antigenicity and consensus N-glycosylation sites to orientate areas of the molecule to the surface folding.

A computer graphics molecular model has been built of the carboxy terminus. The model exhibits remarkable similarity to MHC antigens, and shows particular structural motifs in the correct stereochemical orientation to mimic areas on MHCII molecules recognized by the T cell receptor, possibly in association with CD4.

The structural motifs modelled on putative homologies were allowed to adopt an orientation through standard graphics energy minimization routines and molecular dynamics (DISCOVER) without any forcing of constraints beyond those predicted by algorithms based on empirical data (c. above) and suggested by surface probability (d. above). Therefore, the model approximates to an energetically favorable conformation likely to be taken up by the molecule in solution.

EXPERIMENTAL PROCEDURES

Computer graphics molecular modelling was carried out using a personal Iris 25GT with the Beseem software packages INSIGHT and DISCOVER (Beseem Technologies Ltd, Basingstoke, UK). Protein secondary structure algorithms were from the 'Wisconsin Package' (University of Wisconsin, Biotechnology Centre). In addition the relative probabilities of amino acids being found in α helixes, β strands or β turns were predicted from Chou and Fasman (1974), Biochemistry, 13, 211–245, and Wilmot and Thornton (1988) J. Mol. Biol. 203, 221–232. The amino acid sequences of the following HIV-1 envelope protein precursor molecules were obtained from the Los Alamos database; BH10, BH8, PV22, BRU, MN, SC, SF2, CDC451, WMJ2, RF, MAL, ELI, Z6, Z321, JY1.

The amino acid sequence for one of the HIV isolates, ELI was analyzed by the Wisconsin package and the following data documented: hydrophilicity index (Hopp and Woods, 1981, Proc. Nat. Acad. Sci. 78, 3824–3828; Kyte and Doolittle, 1982, J. Mol. Biol. 157, 105–132), log surface probability (Emini et al., 1985, J. Virol. 55 (3), 836–839; Janin et al., 1978, J. Mol. Biol. 125, 357–386), β turns, α helices and β strands predicted by the Chou-Fasman (C-F; Chou and Fasman, 1974, Biochemistry, 13, 211–245; Chou and Fasman 1978, Adv. Enz. 47, 45–147) and the Garnier-Osguthorpe-Robson (G-O-R; Garnier et al., 1978, J. Mol. Bol. 120, 97–120) algorithms. Only high probability α helices or β strands predicted by both C-F and G-O-R were used in the modelling. Only predicted β turns conserved in several gp120 isolates (Modrow et al., 1987) and those having amino acids of high probability at i, i+1, i+2 and i+3 as given by Wilmot and Thornton (1988), J. Mol. Biol. 203, 221–232, were included. Stereochemistry around the β turns (Wilmot and Thornton, 1990, Protein Engineering 3, 479–493) was not optimized; β type II were constructed where appropriate using the Beseem Editor (MOLEDT). At each stage in the modelling, the transconfiguration of all peptide bonds and the ring geometry of proline residues were checked and the model was subjected to energy minimization.

The carboxy terminal portion of gp120 from amino acid residue 375 to 508 was modelled as follows. Amino acids 375 to 384 were introduced as NC(G)$_6$CN. The cysteines were then forced to a template disulphide bond by tethered energy minimization, the glycines 379–382 were replaced by E-F-F-Y (SEQ ID NO. 17) and the loop energy minimized.

The amino acids 385 to 414 were modelled in MOLEDT with type 1 β bends at i=N 384, 390, 405, 409. The resulting loop has a high surface probability from amino acids 402 to 410 and multiple consensus glycosylation sites (N384, 390, 400, 405, 406, 411). Apart from assuring the surface accessibility of these areas, no further tertiary structure was added.

Amino acids 415 to 443 were modelled by homology with the variable region of immunoglobulin REI (Kieber-Emmons et al., 1989, Biochem. Biophys. Acta. 989, 281–300) obtained from Brookhaven files (Epp et al., 1974, Eur. J. Biochem. 45, 513–524). The gp120 sequence was entered as glycines except for C416, Q420, I422, A433, P434, P435, C442. The loop was modelled by templating C416 to C23 of REI, Q420 to Q27, I422 to 129, A433 to A43 and P434 to P44. The cysteines were then forced to a template disulphide bond by tethered energy minimization.

The linear sequence of amino acids 444 to 484 was subjected to molecular dynamics using the DISCOVER program. This resulted in an area having semi-β strand conformation in the region 446 to 453 and one having semi-helical conformation in the region 471–475 which followed predictions of such structure by the C-F and G-O-R algorithms. Predicted β-turns were then added when these were conserved among gp120 HIV-1 isolates (Modrow et al., 1987, J. Virology 61, 570–578) i.e. type II at i+1=P467 and type 1 at i=N445, N458, R473. The sequence from amino acid residues 453–483 was predicted to have high surface probability and contained concensus glycosylation sites at N458, 459 and 462.

Amino acids 485 to 508 (the predicted site of gp120-gp41 cleavage) were modelled with secondary structure of β strand at 484 to 488 and α helix 496 to 508 (FIG. 4). The latter region coincided with a high surface probability.

RESULTS

Comparison of the amino acid sequences of gp120 with HLA-A2 and DRö

Evidence suggests that the T cell receptor interacts simultaneously with multiple amino acid residues on the α1 and α2-helical stretches of the class I molecule (Bjorkman et al., 1987, Nature 329, 512–518; Ajitkumar et al., 1988, Cell 54, 47–56). For HLA-A2, for which X-ray crystallographic data are available (Bjorkman et al., 1987, Nature 329, 506–512), the amino acids important in the α2 domain are found between 130–180 which includes a minor and major α-helical region. The major α helical region is constrained by the disulphide bond from C101 to C164. The equivalent predicted T cell recognition site of class II MHC (Brown et al, 1988, Nature 332, 845–850; Reinsmoen and Bach, 1990, Hum. Immunol. 27, 51–72; Termijtelen, 1990, Hum. Immunol. 28, 1–10; Ulrich and Atassi, 1990, Eur. J. Immunol. 20, 713–721) is the β chain sequence from amino acids 25 to 75 (approximately). There is the possibility of disulphide bonding from conserved cysteines around amino acids 15 and 80 equivalent to that of C101 to 164 in HLA-A2.

The sequence between the cysteine residues C101 and C164 of HLA-A2 (Bjorkman et al., 1987, Nature 329, 506–512; Orr et al., 1979, Proc. Natl. Acad. Sci. USA 76, 4395–4399) is shown in Table 1 and compared with proposed homologous sequences in DRβ1 (Fan et al, 1989, Human Immunol., 26, 107–121) and gp120 isolate EL1. The numbering chosen for gp120 HIV-1 isolates is shown as homologous with N19 of HLA-DRβ. The other homologous pairing suggested by Brinkworth for DQβ1 (Life Sciences 45, 20 iii-ix) and gp120 isolate WMJ1 are not so apparent when DRβ and gp120 isolate ELI are compared, but the sequences are similar enough to suggest that the gp120 gene may have incorporated coding for this region of HLA-class II.

Of additional interest is the location of the a helix from residue 496 of gp120 in the context of amino acid sequence similarities (Table 1) with class II and class I, respectively, of regions AA 442 to 462 and 468 to 477 of gp120.

Comparison of all the regions of gp160 isolate EL1 with high probability of forming α helix, i.e. regions starting from amino acids 61, 81, 99, 266, 496, 556 and 651, shows that the one from residue 496 is that sharing most homology with the α helices of class I and class II predicted to be part of the location of alloepitopic determinants in these molecules, as defined by structure and T cell reactivity (Brown et al., 1988, Nature 332, 845–850; Termijtelen, 1990, Hum. Immunol. 28, 1–10; Reinsmoen and Bach, 1990, Mum. Immunol. 27, 51–72; Kwok et al., 1990, J. Exp. Med. 171, 85–95). In addition, this sequence in gp120 forms an α helix in which the side chains of arginine residues R497, 501, 505 and 508 project from one aspect.

The remaining basic side chains of R500, K499 and K507 are clustered at an approximate 90–180° angle from the first set suggesting high surface accessibility of this side of the helix. The close proximity of this helix to a conserved tryptophan residue (Table 1) which is located in the minor α helix of HLA-A2 (Bjorkman et al., 1987, Nature 329, 506–518) and partially conserved sequences AADM (SEQ ID NO. 18) and GGDM (SEQ ID NO. 19) in HLA-A2 and gp120, respectively, leading up to the minor α-helix of HLA-A2 (Table 1) adds further weight to the importance of this area of the molecule.

Modelling

As can be seen from Table 1, C442 of the gp120 isolate EL1, proposed as part of a sequence homology with C101 of HLA-A2 and C15 of DRβ, does not form a disulphide bond with a cysteine at the end of the predicted α helix as is the case for the MHCI molecule, and proposed for class II (Brown et al., 1988, Nature 332, 845–850; Termijtelen, 1990, Hum. Immunol. 28 1–10). Peptide mapping data for gp120 (Lasky et al., 1987, Science 233, 209–212; Leonard et al, 1990, J. Biol. Chem. 265, 10373–10382) have suggested that C442 either forms a disulphide bond with C416 or C376.

The possibility of disulphide bond migration to account for this discrepancy (Leonard et al., 1990, J. Biol. Chem. 265, 10373–10382) suggests that these cysteine residues are in close proximity in the molecule. The disulphide bond chosen for the first model of gp120 was from C442 to C416 as suggested by Lasky et al., (1987), Science 233, 209–212, which, although at variance with the prediction of Leonard et al., (1990), J. Biol. Chem. 265, 10373–10382, formed a loop which modelled closely on the REI structure (Kieber-Emmons et al., 1989, Biochem. Biophys. Acta. 989, 281–300). This loop has several homologous amino acids within a region highly conserved amongst gp120 isolates and which has been suggested as of importance in CD4 binding (discussed below).

Amino acids homologous between REI and gp120 isolate EL1 were used as a template for modelling as described above. As suggested by Kieber-Emmons et al., (1989), Biochem. Biophys. Acta. 989, 281–300, and by comparison with the sequence homology with DRβ (Table 1) the disulphide bond was formed so that the strands were anti-parallel with reverse geometry.

The remaining cysteine residues in the carboxy terminus at 376 and 383 were disulphide bonded together and located in the model in close proximity to the larger loop. A second model was then constructed in which the disulphide bonds were altered to the model suggested by Leonard et al., (1990), J. Biol. Chem. 265, 10373–10382, and after extensive energy minimization this was then treated in exactly the same way as for Model I.

Modelling of loops containing glycosylation sites

The modelling strategy discussed above gives a loop from amino acids 383–416 (Model I) or 376–442 (Model II) where little tertiary structure could be defined. However, the presence of multiple glycosylation sites conserved between several HIV-1 gp120 isolates at N390, 394, 400 and 405 (Modrow et al., 1987, J. Virology 61, 570–578), is suggestive of a surface location for this region of molecule.

The region from amino acids 454 to 470 is also predicted to form a glycosylated loop accessible on the surface of the molecule. One further conserved glycosylation site, that at N445, was also made surface accessible and modelled as part of a small loop homologous to that proposed in MHCII (Brown et al., 1988, Nature 332, 845–850; Termijtelen, 1990, Hum. Immunol. 28, 1–10) to be stabilized by a β sheet formation in the floor of the antigen combining site. In the case of gp120 there are also complementary predicted β strands in close proximity to this sequence i.e. AA 412–428, 446–452.

Relative orientation of structural motifs

The final model for the C-terminus of gp120 on linking together the amino acid sequences containing the different structural motifs described above and minimization to RMS<0.2 was generated. This model was compared with a view of HLA-A2α2 chain taken from Brookhaven files. A diagnostic representation of these models is given in FIG. 1, drawing a visual comparison between the α-helical regions and β strands in the context of the tryptophan containing loop (in the minor α helical region of HLA-A2) and two loops projecting under the major α helix. The sequence AA 256–268 shows significant sequence homology with sequences in the C terminus of MHC and with a region of MHCII from residue 144 onwards (Young, 1988, Nature 333, 215) i.e.

| HLA | 248 V V P S G Q E Q R Y 257 (SEQ ID NO. 12) |
|---|---|
| DRβ1 | 144 V V S T G L I Q N G 153 (SEQ ID NO. 13) |
| gp120 EL1 | 255 V V S T Q L L L N G 264 (SEQ ID NO. 14) |

The homology between class I and class II continues in this region to the C terminal of HLA-A2α3 (see also Young, 1988, Nature 333, 215).

| HLA-A2 | 259 C H V Q H E G L P K P L 270 (SEQ ID NO. 15) |
|---|---|
| DRβ1 | 175 C Q V F H P S V T S P L 186 (SEQ ID NO. 16) |

DISCUSSION

Any strategy aimed at dissecting the functional activity of related molecules depends on identification of conserved sequence homology. For gp120 many isolates have now been sequenced providing a large data base for comparison. A survey of 12 sequences of the present report and those of Modrow et al., (1987), J. Virology 61, 570–578, shows that apart from considerable homology leading up to and including cysteine residues the only notable regions conserved between all the isolates are as follows:

| 247 Q C T H G I * P + V S T Q L L L N G S L A E * R | or K, + V or I (SEQ ID NO. 5) |
|---|---|
| 432 Y A P P I (SEQ ID NO. 6) | |
| 444 S N I T G * * L T R D G G | * L or I (SEQ ID NO. 7) |
| 468 G G G * M + D N W | * D or N, + R or K (SEQ ID NO. 8) |
| 479 E L Y K Y K V * | * V or I (SEQ ID NO. 9) |
| 488 I E P L G * A P T + A K R R V V ± R E K R A * V or I, | + R or K ± Q or E (SEQ ID NO. 20) |

These sequences include the conserved regions discussed above which have high probability to form β strands (from AA 447 and 480), areas in the so called YAPPI (SEQ ID NO. 6), SNIT (SEQ ID NO. 11) and conserved W loops and the α helix at the carboxy terminus of gp120. It is these areas that have therefore been included in our gp120 modelling aimed at elucidating the structural motifs important in AIDS pathogenesis.

Since AIDS is a species-specific effect HIV-1 infection, relevance must also be attached to those differences in sequence of the same molecules in both virus and host in related species in which this pathology does or does not occur as a consequence of infection. Gp120 from isolates of the immunodeficiency viruses HIV-2 and SIV show limited homology with the above conserved sequences having sequences VVSS (SEQ ID NO. 21), YXPP (SEQ ID NO. 22) and VVKR (SEQ ID NO. 23) at around AA 260, 450 and 570. On the other hand, comparison between MHCII sequences of chimpanzees (Fan et al., 1989, Human Immunol. 26, 107–121), which are infectable but do not show the immunological sequelae of infection, are approximately as variable as differences existing between individual human class II molecules.

A comparison of the sequences of two class I molecules (Orr et al., 1979, Proc. Natl. Acad. Sci. USA 76, 4395–4399; Amer. Chem. Soc. 18, 5711–5720) was also made to ensure that areas considered to have homology between HIV-gp120 isolates were conserved. This includes the region having a high potential for α-helical formation leading up to the cysteine residue at around C164, the TAADM (SEQ ID NO. 24) sequence, and the conserved tryptophan between these two areas.

Other sequence comparisons which can be considered in respect of the model are those amino acid residues suggested to be important in CD4 binding. The gp120 binding site for CD4 has been mapped primarily to the sequence in the approximate region AA 426–443 using the numbering adopted herein for ELI (the YAPPI (SEQ ID NO. 6) loop) with the alanine at 430 identified as one of the critical residues (Lasky et al., 1987, Science 233, 209–212). Mutations of the tryptophan equivalent to valine 425 in ELi were found to abolish CD4 binding (Cordonnier et al., 1989, Nature 340, 571–574). However, point mutations in the first 150 acids of the amino terminus also affect CD4 binding, and conformational stability of gp120 (Hemming et al., 1989, Arch. Virol. 109, 269–276). This cysteine residue is also conserved residue is also conserved in HIV-2 and SIV seven residues to the carboxy terminus of YXPP (SEQ ID NO. 22).

Nygren et al., (1988), Proc. Natl. Acad. Sci. USA 85, 6543–6546, and Kowalski et al., (1987), Science 237, 1351–1355, have also proposed residues equivalent to those from AA 350 to 477 in our model to be important for CD4 binding. These regions containing the putative CD4 binding site include the two regions which modelled as loops lying under the α helix. For the first of these containing the conserved alanine residue at 430 and YAPPI (SEQ ID NO. 6) sequence, stabilization of the loop is proposed by β sheet formation from the region of high β-strand probability AA 417–422. A second region of high β strand probability AA 446–452 is homologous with a similar region in HLA-DRβ1 (Table 1) proposed in the latter molecule (Brown et al., 1987a). No constraints were used to force the β-strand regions in gp120 into the approximate alignment found.

Alternative disulphide bonding arrangements from C376 and C442 and C383 to C416 as suggested more recently by Leonard et al., (1990), J. Biol. Chem. 265, 10373–10382, do not disrupt the model since the AA 384 to 415 loop has a high degree of flexibility as modelled so far (e.g. without glycosylation) and the close proximity of the disulphide bonds joining C376, 383, 416 and 442 is suggested by the conflicting evidence of disulphide bonding patterns (Lasky et al., 1987, Science 233, 209–212; Leonard et al., 1990, J. Biol. Chem. 265, 10373–10382) and the possibility of disulphide bond migration (Leonard et al., 1990, J. Biol. Chem. 265, 10373–10382).

The important features of the model are therefore likely to be the orientation of a β-sheet area bordered by an α helix in the correct orientation to the conserved tryptophan containing region. Support for the relevance of this model of gp120 are the areas of hydrophilic amino acid side chains and potential carbohydrate chains projecting along the 'bottom' of the molecule from the α helix (R497, 500, 501, 505 and 508) and the second loop (N458, 459, 462 and K482, 484).

EXAMPLE 7

Analysis of Modelling Results

FIG. 1 shows the α-carbon backbone of the carboxy terminus of gp120 folded as determined by molecular modelling (Example 6) and the α2 chain of HLA-A2 (MHC1) taken from X-ray coordinate data.

The similarities shown in the orientation of the α-helix, β-strands and homologous sequences in the region called the minor α-helix of MHCII are particularly remarkable as the HLA-A2 molecule was at no time used as a template to force the folding of gp120. Most importantly the α-helix of gp120 has sequence homologies with the non-polymorphic amino acids of the major α-helices of MHCI and class II which make up the alloepitope recognized by the TCR (underlined).

Class I: 152 Val AlaGlu GlnLeu ArgAla TyrLeu Glu Gly ThrCys Val 165 (SEQ ID NO. 25)

Class II: 68 Leu LeuGlu GlnArg ArgAla AlaVal Asp ThrTyr CysArg 81 (SEQ ID NO. 26)

The orientation of the underlined residues in the MHCI and II sequences is shown in FIGS. 2 and 3 (to fit with published diagrams of MHC the carboxy terminus is shown on the left, whereas amino acid sequences are written from N to C terminus—other amino acids are shown as alanines).

FIGS. 4 and 5 show two different faces of the gp120 helix, the latter shown interacting with an anionic ligand of the invention suitable as an inhibitor of T cell recognition of gp120, CD4 binding and gp120-gp41 cleavage. FIG. 4 shows the orientation of the amino acid side chains which mimic the class II sequence (FIG. 3). FIG. 5 shows the additional basic amino acid side chains of gp120.

Class II: 68 Leu LeuGlu GlnArg Arg AlaAla Val AspThrTyrCys Arg 81 (SEQ ID NO. 26)

gp120: 496 ThrLysAlaLys Arg ArgValVal Gln ArgGluLys Arg 508 (SEQ ID NO. 27) (most isolates)

The underlining in the upper chain shows the homologies of upper and lower chains, while the underlining in the lower chain shows the relative position of the face of the two chains.

The relative orientation of the two sets of side chains is shown in FIG. 6 looking along the α-helix from the carboxy terminus. The distances between these side chains can be used to design ligands such as that in FIG. 5 based on a sulphated sugar polymer which can interact with the specified residues. The high probability of the surface and TCR accessibility of this α-helix makes it a target not only for rational drug therapy but also immunotherapy and diagnosis.

The most common sequence for the α-helix of gp120 which mimics the major α helix of MHC important in T cell recognition is as follows (shown above for gp120 as three letter code):

T K A K R R V V Q R E K R 508 (SEQ ID NO. 27)

The common alternatives (including that in isolate ELI) are:

T R A K R R V V E R E K R (SEQ ID NO. 29)
    K         Q              508

That sequence which has E at residue 504 (underlined) is most like class I/class II (E and D here, respectively). Both class I and class II have the equivalent of R500 (underlined) and class II has the equivalent of R508 on the same face of the helix.

Uses of different Sequences

Various sequences corresponding to gp120 residues 496–508 can be used for different end-purposes.

a) In order to demonstrate that gp120 can (i) form an α-helix in this region, and (ii) mimic MHC, the following sequence is synthesized:

T K A K R R V V E R E K $R_{508}$ (SEQ ID NO. 1)

b) For use as an immunogen to raise antibodies in mice as a pilot for a potential vaccine, the following is preferred which will cross-react least with MHCI or II (R500 and 508 are replaced by A), but has a strong likelihood of forming an α-helix in solution and has a tail ($A_{509}$ the first amino acid of gp41) for attachment of immune adjuvants i.e.

T K A K A R V V Q R E K A $A_{509}$ (SEQ ID NO. 30)

However, to raise anti-idiotypic antibodies reactive with the T cell receptor Vβ subsets important in AIDS, the MHC mimic would have to be used as the original immunogen i.e.

T K A K R R V V E R E K R $A_{509}$ (SEQ ID NO. 31)

c) For studies of polyanionic ligand binding the following two sequences will initially be used in the modelling strategy

T K A K R R V V E R E K R A (SEQ ID NO. 31)

T R A K R R V V E R E K R A (SEQ ID NO. 32)
497 501 505 508

The underlined residues are the conserved basic amino acids which occur on one face of the α-helix but are not those important in normal MHC-T cell function.

At the risk of impairing normal function but having a ligand for which mutants will not be able to cause AIDS, the additional MHC-type basic residues R500 and R508 can be included in the design of the polyanion (together with Q/E 504, the residues R500 and R508 form a second face of the helix proposed to react directly with the T cell receptor. The proximity of the side chains of these residues to the R497-R501-R505 face gives additional evidence for our hypotheses).

FIGS. 7 and 9 show the last sequence above as a 5-fold helix. FIGS. 5 and 10 illustrate the distances between side chains.

These distances are of the same order of magnitude as sulphate groups spaced variously around the hydroxyl groups of mono- to trisaccharides (FIG. 8). The correct ligands can be designed to interact specifically with R497-R501-R505 alone or all six amino acids as described in c) above.

EXAMPLE 8

Specific gp120 Ligands based on Oligosaccharide Sequences

Suitable starting materials are generally widely available and naturally occurring mono-, di-, tri- or tetrasaccharides. Additional monosaccharides can be added by standard glycosidic bond formation reactions (such as by reaction 1 in the scheme below).

Suitable starting materials may be selected so as to give the correct stereochemistry of functional groups.

Blocking of specific hydroxyl groups which are not required to be in sulphated form, may be achieved by selective 4, 6-di-O-benzylidation (such as described in reaction 2), 6-O-benzoylation (such as described in reaction 3) or 6-O-tritylation and O-acetylation (such as described in reaction 4) as required (depending on the conditions of synthesis and removal). Sulphation may be performed as described in reaction 5.

REACTION SCHEME

Reaction 1: Selective trans glycosylation

Two suitably protected monosaccharide or oligosaccharide derivatives, such as per-O-acetylated N-acetyllactosamine bromide and 4, 6-di-O-benzylidene methyl mannopyranoside as a specific example (1–2 gms) are reacted at −15° C. with silver trifluoromethanesulphonate (2.2 gms, 8.63 mmol) and 2, 4, 6-collidene (1.05 gms) in dichloromethane (20 ml). The mixture is stirred at room temperature for 16 hrs and then washed with sodium bicarbonate and evaporated to dryness.

Reaction 2: 4, 6-di-O-benzylidation

To the oligosaccharide (2 gms) in solution in dimethylformamide (30 ml) is added barium hydroxide (5.6 gms), barium hydroxide octahydrate (5.9 gms) and benzyl bromide (5.3 gms). The mixture is stirred for 16 hrs at room temperature, diluted with ethyl acetate (50 ml) washed with water and evaporated to dryness. When required, the group can be removed by heating gently in dilute acid.

Reaction 3: Selective 6-O-benzoylation

To the sample (1 gm) in dichloromethane (20 ml) is added n-benzoylimidazole (2.2 gms). The mixture is stirred at room temperature for 16 hrs and the product extracted into water and evaporated to dryness. This group is removed in mild base whereas the 6-O-trityl group is removed in mild acid.

Reaction 4: O-acetylation

To the sample (1 gm) in pyridine (20 ml) at 0° C. is added acetic anhydride (5 ml). The mixture is stirred for 16 hrs at 0° C. and then evaporated to dryness and re-evaporated over toluene. This group can be removed by treatment with a catalytic quantity of sodium methoxide in methanol with stirring at room temperature for 2 hrs (mild base).

Reaction 5: Sulphation

To a stirred solution of the protected oligosaccharide (1 gm) in dry pyridine (5 ml) is added sulphur-trioxide-pyridine complex (1 gm) in aliquots. The mixture is kept overnight at room temperature, the pH adjusted to 9 with molar KOH and the mixture stirred for 2 hrs before the product is extracted with hot methanol.

The deprotected sulphated oligosaccharide is purified by anion exchange high performance liquid chromatography (e.g Varian AX-5 column 10×250 mm) using a 10 mailer gradient of potassium phosphate followed by desalting on a Biogel P4 column eluted in water.

Example of the Synthesis of a Gp120 Ligand (A) 2-Acetamido-3, 6-di-O-acetyl-4-O-(2, 3, 4, 6-tetra-O-acetyl-β-D-galactopyranosyl)-1-thiomethyl-α/β-D-glucopyranoside

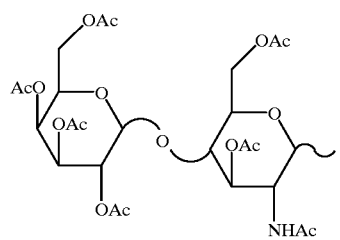

(per-O-acetylated N-acetyllactosamine)
[Reaction 4]

(B) 4,6-Di-O-benzylidene-1-O-methyl-α/β-2-mannopyranoside

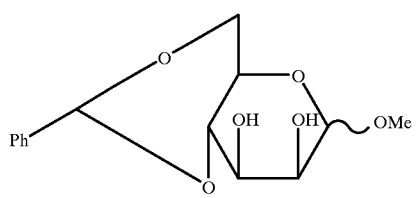

(4,6-O-benzylidene methylmannopyranoside
[Reaction 2]

(i) Glycosidic bond formation
(ii) Deprotection (mild acid to remove the benzylidene group and mild base to remove acetyl groups).
(C) O-β-D-Galactopyranosyl-(1-4)-O-β-D-2-acetamido-2-deoxyglucopyranosyl-(1-2)-Oα/β-D-1-O-methylmannopyranoside (plus O-β-D-galactopyranosyl-(1-4-O-β-D-acetamido-2-deoxyglucopyranosyl-(1-3)-O-α/β-D-1-O-methylmannopyranoside).

The following steps were performed as described above.
(i) selective 6-O-tritylation;
(ii) peracetylation;
(iii) removal of trityl group;
(iv) 6-O-sulphation; and
(v) removal of O-acetyl groups.

(D) O-β-D-6-O-Sulphate-galactopyranosyl-(1-4)-O-β-D-2-acetamido-2-deoxy-6-O-sulphate-glucopyranosyl-(1-2)-O-α/β-D-1-O-methylmannopyranoside (plus O-3-D-6-O-sulphate-galactopyranosyl-(1–4)-O-β-D-2-acetamido-2-deoxy-6-O-sulphateglucopyranosyl-(1-3)-O-α/β-D-1-O-methylmannopyranoside)

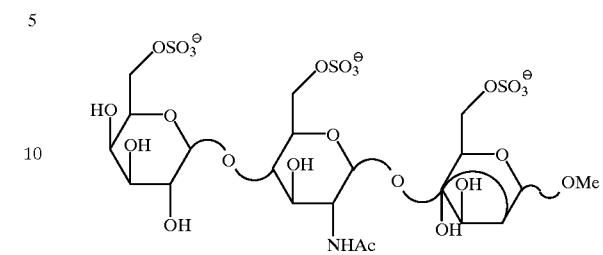

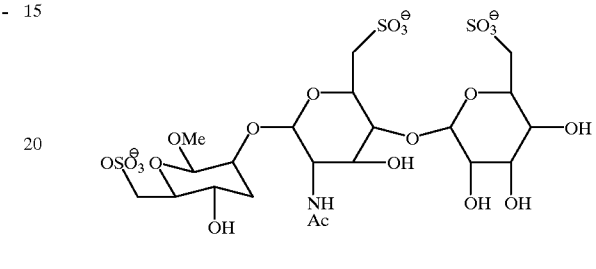

Figure 5:
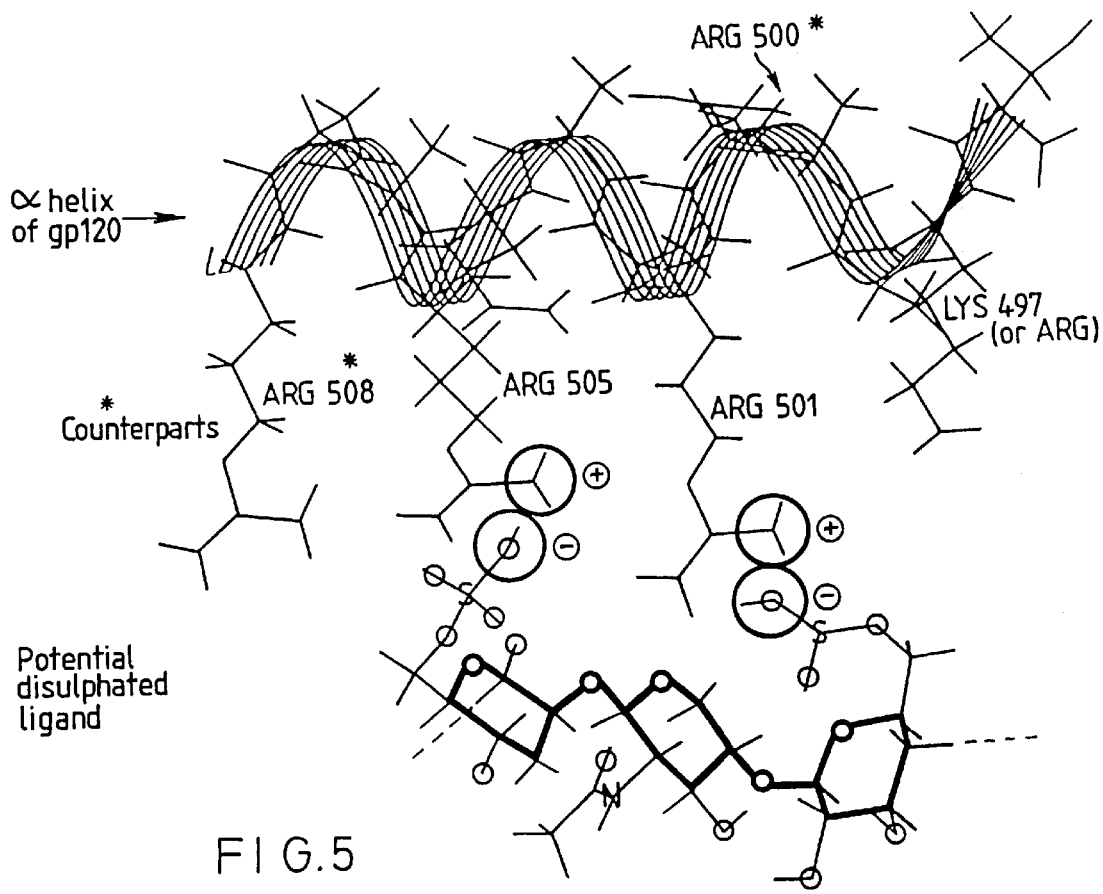
FIG. 5 is a computer-generated diagrammatic view of the α-helix of gp120 showing basic amino acid sidechains contained therein.
Figure 6:
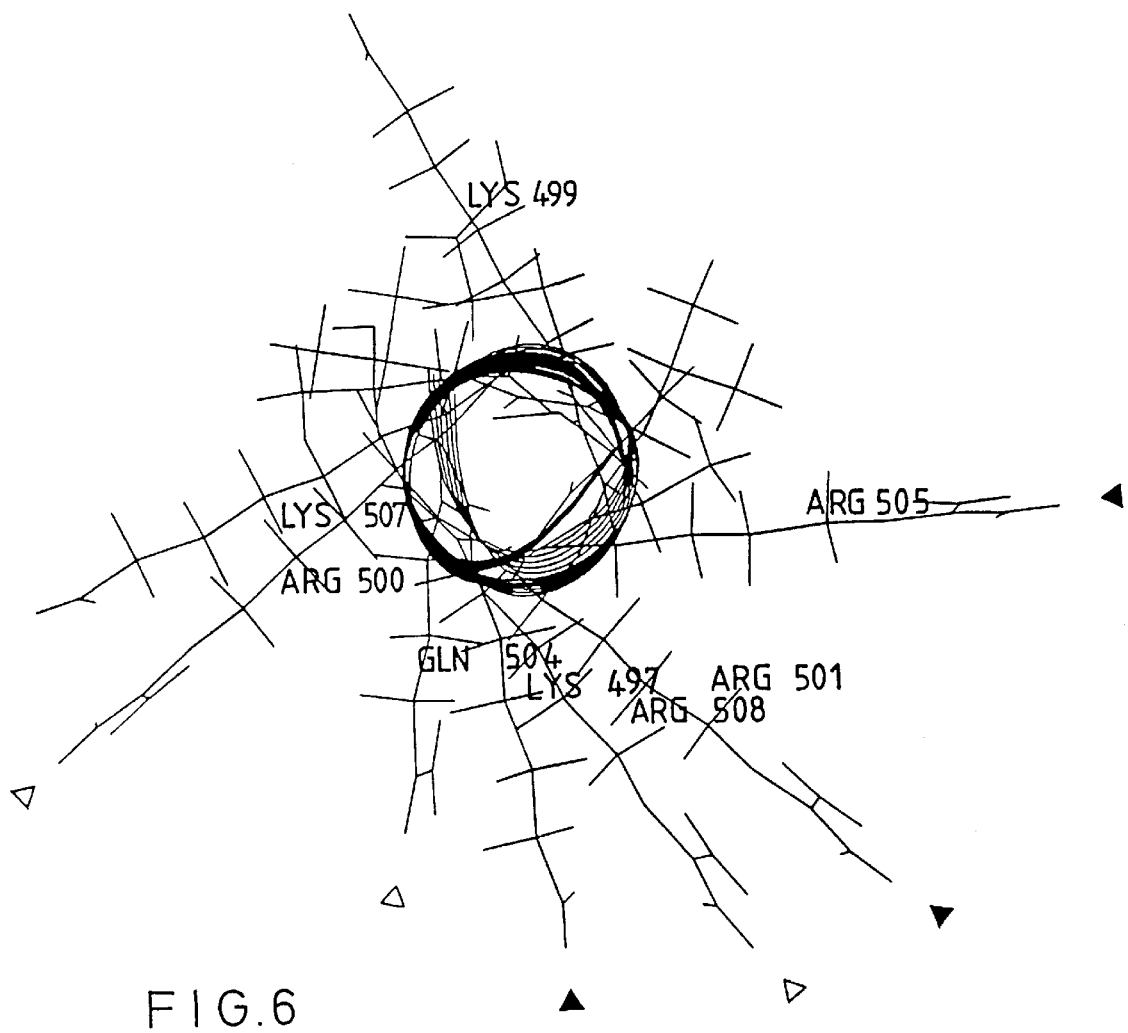
FIG. 6 is a diagrammatic representation of the sidechains of class II MHC glycoprotein and gp120 viewed along the α-helix from the carboxy terminus.
Figure 7:
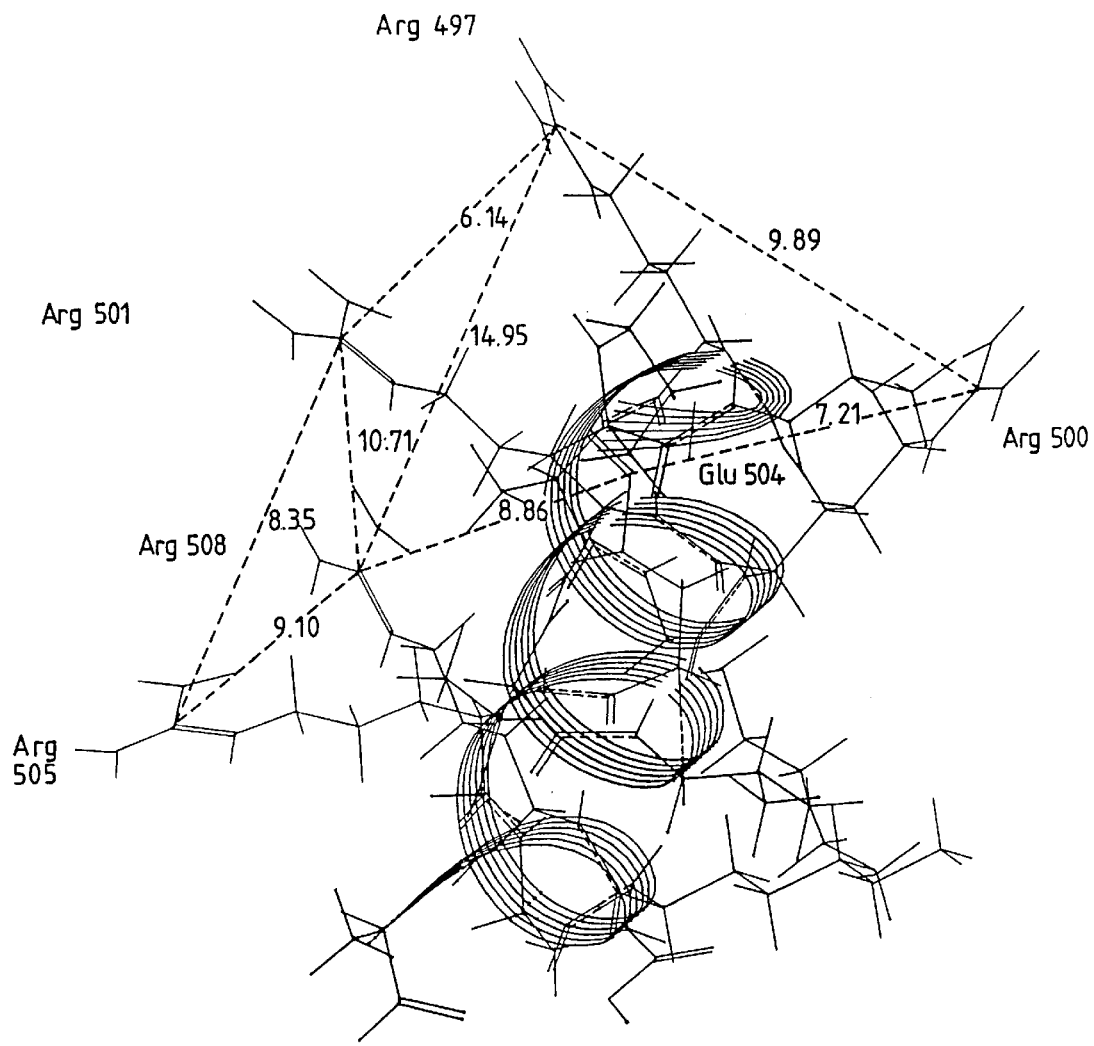
FIG. 7 is a computer-generated representation of the gp120 sidechain of residue 496–509 conformed as a five-fold helix.
Figure 8:
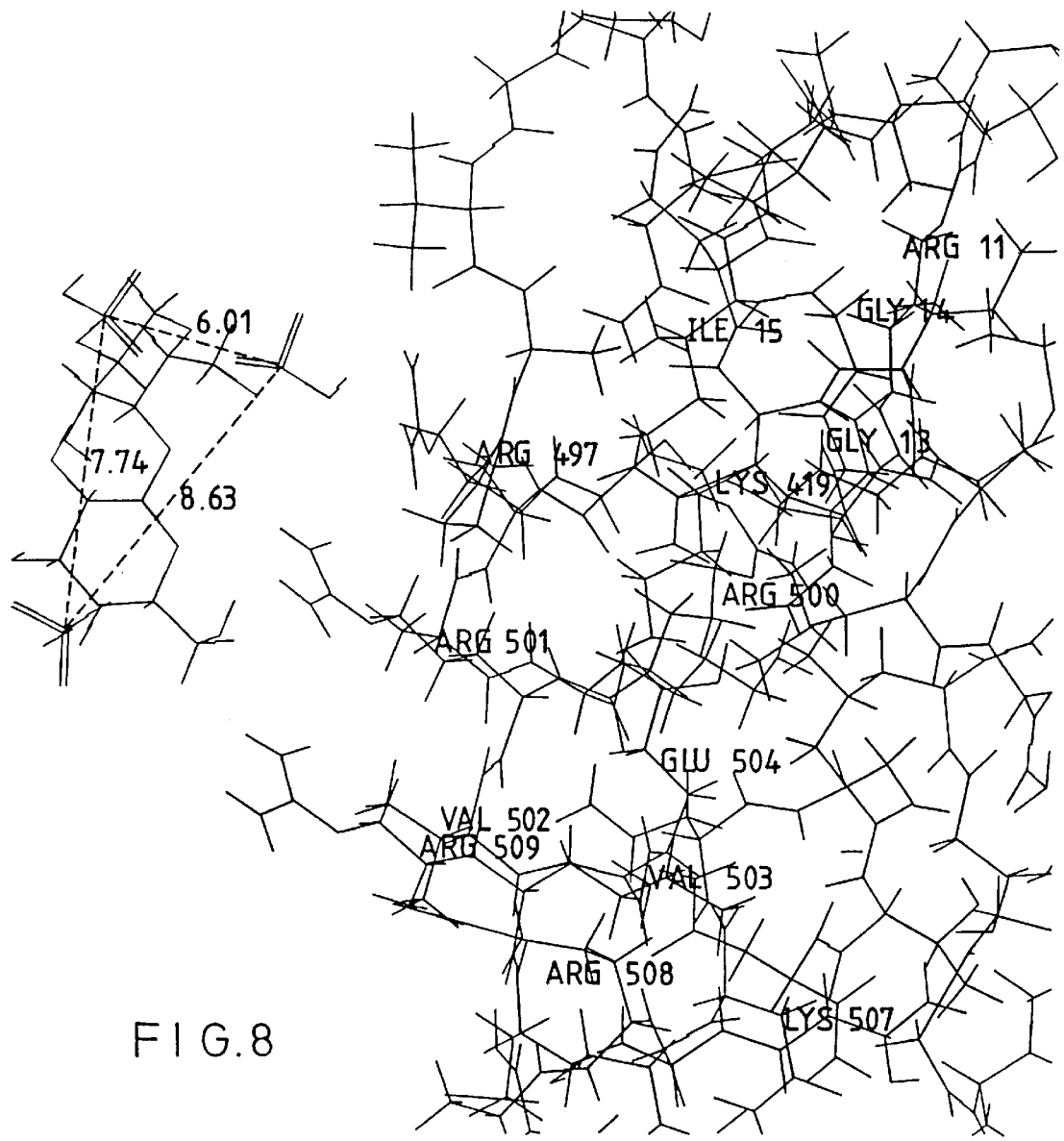
FIG. 8 shows an alternate representation of the amino acids of the sequence of FIG. 7.

This compound is as shown in the accompanying FIG. 5.

Alternative Example of a Gp120 Ligand

Chitin [Sigma Chemical Co. Ltd.] is used for oligomers of the general formula 4-O-(2-acetamido, 2-deoxy-)-α-D-glycopyranose)$_n$.

Chitin may be per-O-acetylated by the methods described above, and then treated with a mixture of 35:15:1 v/v acetic anhydride/glacial acetic acid/concentrated sulphuric acid to yield the oligomer wherein n=5 or 6. This is then purified and treated to remove the acetyl groups to give [4-O(2-deoxy-2-acetamide-β-D-glucopyranose]$_5$.

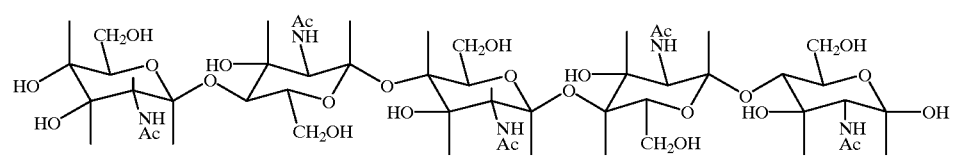

Selective benzoylation of the CH$_2$OH group
(6-O-benzoylation)

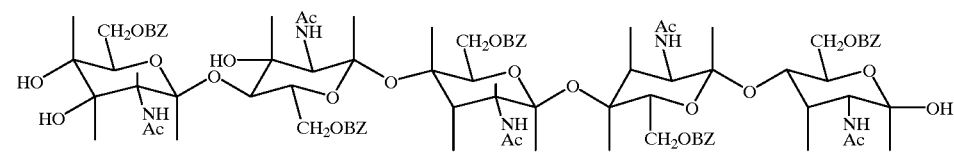

Sulphation followed by removal of the benzoyl groups using a catalytic amount of sodium methoxide in methanol, room temperature 2 hrs (mild base)

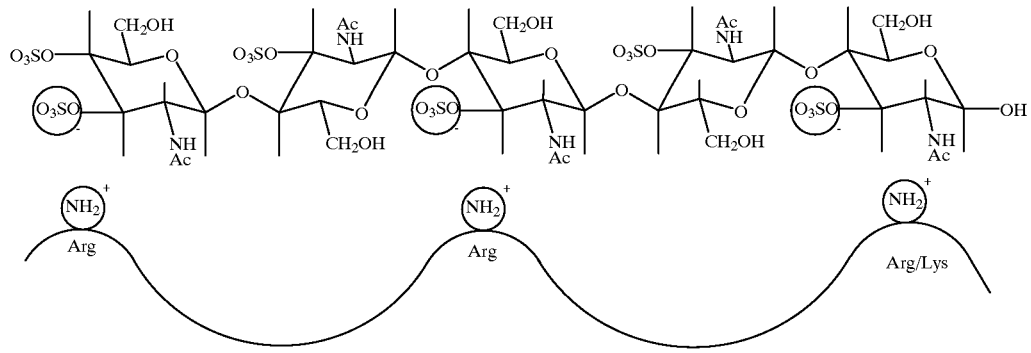

EXAMPLE 9

Peptide synthesis

Peptides bearing sequences homologous to the proposed C terminal α-helix of gp120 may be synthesized as described below.

Peptides are synthesized on an automated peptide synthesizer under the conditions specified by the manufacturer, such as Applied Biosystems, using HMP resin and suitably protected N-α-fluorenylmethoxy-carbonyl (FMOC) amino acids activated by 2-(1-H-benzotriazol-1-yl)-1,1,3,3-tetramethyluronium hexafluorophosphate. The finished peptide is cleaved from the resin and deprotected with 82.5% trifluoroacetic acid/5% phenol/5% thioanisole/2.5%, 1,2-ethanediol/5%, water for 1.5 hrs. The crude peptide is isolated by ether precipitation and centrifugation and then purified by high performance liquid chromatography on a Dynamex C-8 column, 300 A pore size, 10×250 mm using a gradient from 12–20% 0.1% trifluoracetic acid/acetonitrile over 20 mins. Peptide containing fractions are pooled and freeze-dried. These are analyzed for sequence and conformation by amino acid sequencing, mass spectrometry and nuclear magnetic resonance spectroscopy, as known in the art.

EXAMPLE 10

Induction of Allogeneic Response by Gp120 Peptide

A peptide of the sequence: T K A K R R V V E R E K R (SEQ ID NO. 1) was found to induce an allogeneic response in a cell culture system and was recognized by antibodies and T cells of HIV+ patients.

Allogeneic response in cell culture.

The system was as follows:

ANTIGEN CONTROLS

1. Peripheral blood lymphocytes from one individual (Self) are stimulated to grow in the presence of Antigen Presenting Cells from the same individual (Self) presenting influenza peptide antigen and expanded with IL-2 over two weeks.

2. Other Self cells expressing influenza antigen are immortalized with EBV and used as target cells.

3. Other Self cells expressing another antigen are immortalized with EBV and used as target cells.

Positive Control

4. The Self lymphocytes from stage 1 now containing Cytotoxic T Lymphocytes specific for influenza are added to Self cells from stage 2 and specifically kill the target cells expressing influenza antigen.

Negative Control

5. The Self lymphocytes from stage 1 now containing Cytotoxic T Lymphocytes specific for influenza are added to Self cells from stage 3 and have no effect on the target cells expressing another antigen.

Allogeneic Control

6. Peripheral blood lymphocytes from one individual (Self) are stimulated to grow in the presence of Antigen Presenting Cells from the another individual (Non-Self) presenting influenza peptide antigen and expanded with IL-2 over two weeks.

Allogeneic Positive Control

7. The lymphocytes from stage 6 now containing non-specific Cytotoxic Self T Lymphocytes are added to Self cells from stage 3 and non specifically kill the target cells expressing other antigens.

EXPERIMENT

8. Peripheral blood lymphocytes from one individual (Self) are stimulated to grow in the presence of Antigen Presenting Cells from the same individual (Self) exposed to peptide T K A K R R V V E R E K R (SEQ ID NO. 1) and expanded with IL-2 over two weeks.

9. The lymphocytes from stage 8 containing non-specific Cytotoxic T Lymphocytes are added to cells from stage 3 and non-specifically kill the target cells expressing other antigens in a similar manner to the allogeneic control.

Peptide T K A K R R V V E R E K R (SEQ ID NO. 1) (corresponding to the major α-helix on gp120) induces an allogeneic response between self lymphocytes and self target cells. This demonstrates that this peptide alone can mimic the mechanism of AIDS induced by HIV. Repeated administration of the peptide (and related peptides) should attenuate the response of the patient's immune system to both this peptide and the alloepitope on HIV and, therefore, prevent AIDS (attenuation of an immune response by repeated administration of a peptide is known).

The lymphocytes from four out of six individuals (HIV negative) respond to the peptide in this system indicating that this system can also be used as a diagnostic test to distinguish between individuals who respond to HIV and will develop AIDS and those who are resistant to AIDS.

18 out of 20 HIV + patients have clear antibody responses and T cell responses to the peptide.

The above results and those of the Table below show that the peptide can be used as a vaccine, and that it is capable of eliciting an allogeneic response when associated with the membrane of antigen presenting cells.

TABLE

| | ALL E:T dilutions = 60:1; 30:1; 15:1; 7:1 | | | |
|---|---|---|---|---|
| Donor | FLU/FLU | ALLO/ALLO | FLU/SELF | ALLO/SELF |
| A | 17;12;8;12 | 34;29;20;15 | 5;4;4;3 | 0;0;0;0 |
| B | 15;8;3;2 | 16;6;0;0 | 0;0;0;0 | 3;0;0;0 |
| c | 9;0;0;0 | 44;33;16;18 | 0;0;0;1 | 0;0;0;0 |
| D | 9;5;4;7 | 34;28;11;0 | 0;0;0;0 | 14;0;0;0 |
| F | 60;28;17;8 | 40;27;19;0 | NOT TESTED | 4;0;0;0 |
| F | 4;0;0;0 | 36;16;8;4 | NOT ThSTED | 13;3;0;0 |

| Donor FLU/ PEP- TIDE | ALLO/ PEP1× | ALLO/ PEP10× | ALLO + IL-2/ PEP 1× | ALLO + IL-2 PEP 10× |
|---|---|---|---|---|
| A | 2;1;0;2 | 15;6;0;4 | NOT TESTED | NOT TESTED | NOT TESTED |
| B | 0;1;0;0 | 14;3;0;6 | 16;15;0;2 | 18;5;4;2 | 19;14;6;6 |
| C | 0;0;0;0 | 0;0;0;0 | 22;16;12;6 | 4;0;0;0 | 16;13;5;0 |
| D | 0;0;0;0 | 21;16;6;0 | 31;16;3;2 | 17;8;0;0 | 31;19;4;3 |
| E | 14;0;0;0 | 4;0;0;0 | 1;0;0;0 | 19;8;0;0 | 27;15;11;5 |
| E | 0;0;0;0 | 14;0;0;0 | 18;6;5;2 | 8;0;0;0 | 32;18;9;19 |

1× = 2.5 µM/ml;
10× × 25 µM/ml

EXAMPLE 11

Vaccine

A vaccine is prepared from the peptide of Example 10 according to the following:

| | |
|---|---|
| Peptide | 1–200 µg |
| Saline | 0.5 ml |
| Alum (adjuvant) | optional |

The above formulation may be used for intramuscular or subcutaneous administration, as required, or may be modified for other routes of administration as suitable.

Dosing may be up to 8 times over 6 months, for example, although more or less doses may be required according to the age and condition of the patient.

---

What is claimed is:

1. A peptide consisting of:

T R A K R R V V E R E K R (SEQ ID No. 4)

wherein said peptide will stimulate proliferation of a T-cell clone in a T-cell proliferation assay and wherein said peptide will produce an alloepitopic effect in a second T-cell assay comprising said stimulated T-cell clone such that said T-cell clone proliferates and further wherein said peptide when administered in a tolerizing amount will suppress proliferation of said T-cell clone in said second assay.

2. A peptide consisting of:

T R A K R R V V Q R E K R (SEQ ID No. 29)

wherein said peptide will stimulate proliferation of a T-cell clone in a T-cell proliferation assay and wherein said peptide will produce an alloepitopic effect in a second T-cell assay comprising said stimulated T-cell clone such that said T-cell clone proliferates and further wherein said peptide when administered in a tolerizing amount will suppress proliferation of said T-cell clone in said second assay.

3. A peptide consisting of:

T K A K R R V V E R E K R (SEQ ID No. 1)

wherein said peptide will stimulate proliferation of a T-cell clone in a T-cell proliferation assay and wherein said peptide will produce an alloepitopic effect in a second T-cell assay comprising said stimulated T-cell clone such that said T-cell clone proliferates and further wherein said peptide when administered in a tolerizing amount will suppress proliferation of said T-cell clone in said second assay.

4. A peptide consisting of:

T K A K R R V V Q R E K R (SEQ ID No. 27)

wherein said peptide will stimulate proliferation of a T-cell clone in a T-cell proliferation assay and wherein said peptide will produce an alloepitopic effect in a second T-cell assay comprising said stimulated T-cell clone such that said T-cell clone proliferates and further wherein said peptide when administered in a tolerizing amount will suppress proliferation of said T-cell clone in said second assay.

5. A peptide consisting of:

T K A K R A V V E R E K R (SEQ ID No. 20)

wherein said peptide will stimulate proliferation of a T-cell clone in a T-cell proliferation assay and wherein said peptide will produce an alloepitopic effect in a second T-cell assay comprising said stimulated T-cell clone such that said T-cell clone proliferates and further wherein said peptide when administered in a tolerizing amount will suppress proliferation of said T-cell clone in said second assay.

6. A peptide consisting of:

T R A K R R V V E R E K R A (SEQ ID No. 32)

wherein said peptide will stimulate proliferation of a T-cell clone in a T-cell proliferation assay and wherein said peptide will produce an alloepitopic effect in a second T-cell assay comprising said stimulated T-cell clone such that said T-cell clone proliferates and further wherein said peptide when administered in a tolerizing amount will suppress proliferation of said T-cell clone in said second assay.

7. A peptide consisting of:

T K A K R R V V E R E K R A (SEO ID No. 31)

wherein said peptide will stimulate proliferation of a T-cell clone in a T-cell proliferation assay and wherein said peptide will produce an alloepitopic effect in a second T-cell assay comprising said stimulated T-cell clone such that said T-cell clone proliferates and further wherein said peptide when administered in a tolerizing amount will suppress proliferation of said T-cell clone in said second assay.

8. A peptide consisting of:

T K A K R A V V E R E K R A (SEQ ID No. 20)

wherein said peptide will stimulate proliferation of a T-cell clone in a T-cell proliferation assay and wherein said peptide will produce an alloepitopic effect in a second T-cell assay comprising said stimulated T-cell clone such that said T-cell clone proliferates and further wherein said peptide when administered in a tolerizing amount will suppress proliferation of said T-cell clone in said second assay.

9. An immunogenic composition comprising:

(a) a peptide selected from the group consisting of:

T R A K R R V V E R E K R (SEQ ID No. 4)

T R A K R R V V Q R E K R (SEQ ID No. 29)

T K A K R R V V E R E K R (SEQ ID No. 1)

T K A K R R V V Q R E K R (SEQ ID No. 27)

T K A K R A V V E R E K R (SEQ ID No. 20)

T R A K R R V V E R E K R A (SEQ ID No. 32)

T K A K R R V V E R E K R A (SEQ ID No. 31);

and

T K A K R A V V E R E K R A (SEQ ID No. 20)

and;

(b) an acceptable adjuvant or carrier protein.

* * * * *

UNITED STATES PATENT AND TRADEMARK OFFICE
CERTIFICATE OF CORRECTION

PATENT NO.    : 5,935,579                                             Page 1 of 1
DATED         : August 10, 1999
INVENTOR(S)   : Habeshaw et al.

It is certified that error appears in the above-identified patent and that said Letters Patent is hereby corrected as shown below:

U.S. PATENT DOCUMENTS,
5,773,573    6/30/98    Rupert Holms

Signed and Sealed this

Eighth Day of January, 2002

Attest:

JAMES E. ROGAN
Attesting Officer    Director of the United States Patent and Trademark Office